US007728115B2

(12) United States Patent
Arepally et al.

(10) Patent No.: US 7,728,115 B2
(45) Date of Patent: *Jun. 1, 2010

(54) COMPOSITIONS AND METHODS USEFUL FOR THE DIAGNOSIS AND TREATMENT OF HEPARIN INDUCED THROMBOCYTOPENIA/THROMBOSIS

(75) Inventors: Gowthami M. Arepally, Durham, NC (US); Walter Kisiel, Albuquerque, NM (US); Keiko Kamei, Kumamoto (JP); Shintaro Kamei, Kumamoto (JP)

(73) Assignee: STC. UNM, Albuquerque, NM (US)

( * ) Notice: Subject to any disclaimer, the term of this patent is extended or adjusted under 35 U.S.C. 154(b) by 677 days.

This patent is subject to a terminal disclaimer.

(21) Appl. No.: 11/195,095

(22) Filed: Aug. 2, 2005

(65) Prior Publication Data
US 2006/0040323 A1    Feb. 23, 2006

Related U.S. Application Data

(63) Continuation of application No. 09/615,872, filed on Jul. 13, 2000, now Pat. No. 6,964,854.

(60) Provisional application No. 60/143,536, filed on Jul. 13, 1999.

(51) Int. Cl.
```
C07K 16/18      (2006.01)
C12P 21/08      (2006.01)
G01N 33/564     (2006.01)
G01N 33/577     (2006.01)
C12N 5/20       (2006.01)
```
(52) U.S. Cl. .................. 530/388.7; 435/7.24; 435/69.1; 435/70.21; 435/452; 435/332; 435/337; 435/975; 436/506; 436/512; 436/548; 530/387.3; 530/388.25; 530/866

(58) Field of Classification Search ................ 435/7.24, 435/69.1, 70.21, 452, 332, 337; 436/512, 436/548; 530/387.3, 388.1, 388.15, 388.2, 530/388.25, 388.7, 389.1, 389.3, 389.6, 866
See application file for complete search history.

(56) References Cited

U.S. PATENT DOCUMENTS

| | | | |
|---|---|---|---|
| 4,160,452 A | 7/1979 | Theeuwes | |
| 4,256,108 A | 3/1981 | Theeuwes | |
| 4,265,874 A | 5/1981 | Bonsen et al. | |
| 5,466,582 A | 11/1995 | Amiral | |
| 6,964,854 B1 * | 11/2005 | Arepally et al. | ............ 435/7.24 |

OTHER PUBLICATIONS

Owens et al., 1994. The genetic engineering of monoclonal antibodies. J. Immunol. Meth. 168: 149-165.*
Rudikoff et al., 1982. Single amino acid substitution altering antigen-binding specificity. Proc Natl Acad Sci USA 79: 1979-1983.*
Altschul et al., 1990, *J. Mol. Biol.*, 215:403-410.
Altschul et al., 1997, *Nucleic Acids Res.*, 25:3389-3402.
Amiral et al., 1992, *Thrombosis & Haemostasis*, 68(1):95-96.
Amiral et al., 1996, *Am. J. Hematol.*, 52:90-95.
Amiral et al., 1996, *Blood*, 88:410-416.
Amiral et al., 1996, *Br. J. Hematol.*, 92:954-959.
Arepally et al., 1995, *Am J Clin. Pathol.*, 104:648-654.
Arepally et al., 1997, *Blood*, 89:370-375.
Arepally et al., 1998, *Clinical Reviews in Allergy and Immunology*, 16:237-247.
Arepally, "Characterization of a monoclonal antibody to PF4/heparin (KKO) with functional and serologic properties of HIT antibodies", *Blood*, Nov. 15, 1999; 94(10).
Arepally et al., "Characterization of a murine monoclonal antibody that mimics heparin-induced thrombocytopenia antibodies", *Blood*, Mar. 1, 2000;95(5):1533-1540, Mar. 1, 2000.
Arepally et al., "Antibodies from patients with heparin-induced thrombocytopenia stimulate monocytic cells to express tissue factor and secrete interleukin-8", *Blood*, Aug. 15, 2001;98(4):1252-1254.
Arepally et al., "Pathogenesis of heparin-induced thrombocytopenia and thrombosis", *Autoimmun. Rev.*, May 2002;1(3):125-132.
Ausubel et al., *Current Protocols in Molecular Biology*, John Wiley & Sons, New York, NY, 1994; title page, copyright page and table of contents only; 14 pgs.
Bachelot-Loza et al., 1998, *Thromb. Haemost.*, 79:523-528.
Baggiolini et al., 1989, *J. Clin. Invest.*, 84:1045-1049.
Barbas, 1995, *Nature Medicine*, 1:837-839.
Bauer et al., 1997, *Circulation*, 95:1242-1246.
Bird et al., 1988, *Science*, 242:423-426.
Blank et al., 1997, *Clin. Exp. Immunol.*, 108(2):333-339.
Blank, et al., "A mouse model for heparin-induced thrombocytopenia", *Seminars in Hematology*, Jan. 1999;36(1):12-16, Jan. 1999.
Bork et al., "Go hunting in sequence databases but watch out for the traps", *Trends in Genetics*, Oct. 1996;12(10):425-427.
Bork, "Powers and pitfalls in sequence analysis: the 70% hurdle", *Genome Research*, Apr. 2000;10(4):398-400.
Boshkov et al., 1993, *Br. J. Haematol.*, 84:322-328.
Brenner, "Errors in genome annotation", *Trends in Genetics*, Apr. 1999;15(4):132-133.

(Continued)

*Primary Examiner*—Shafiqul Haq
*Assistant Examiner*—James L Grun
(74) *Attorney, Agent, or Firm*—Mueting Raasch & Gebhardt, P.A.

(57) ABSTRACT

The invention includes compositions, kits and methods comprising a monoclonal antibody which shares key functional properties with the polyclonal antibodies which participate in the pathogenesis of heparin induced thrombocytopenia/thrombosis (HIT/HITT) in a mammal. The monoclonal antibody of the invention preferentially binds with a PF4/heparin complex relative to the binding of the antibody with PF4 or heparin alone. The monoclonal antibody of the invention also binds specifically with PF4 in a complex with other glycosaminoglycans besides heparin, and also activates platelets. The monoclonal antibody of the invention is useful in methods for diagnosing and treating HIT/HITT in a mammal. A humanized version of the monoclonal antibody of the invention is also included, along with a process for humanizing the monoclonal antibody of the invention.

4 Claims, 10 Drawing Sheets

OTHER PUBLICATIONS

Burton et al., 1994, *Adv. Immunol.*, 57:191-280.
Carlsson et al., 1998, *Blood*, 92:1526-1531.
Carter et al., 1992, *Bio/Technology*, 10:163-167.
Chong et al., 1993, *Blood*, 81:988-993.
Chong, 1995, *British Journal of Haematology*, 89:431-439.
Ciaglowski, et al., "Monoclonal antibodies to bovine platelet factor 4: species interactions to platelets and megakaryocytes using indirect immunocytofluorescence", *Thrombosis Research*, 41(6), Mar. 15, 1986.
De Kruif et al., 1995, *J. Mol. Biol.*, 248:97-105.
De Reys et al., 1993, *Blood*, 81:1792-1800.
Deutscher et al., *Guide to Protein Purification*, Harcourt Brace Jovanovich, San Diego, CA, 1990; title page, copyright page and table of contents only; 4 pgs.
Doerks et al., "Protein annotation: detective work for function prediction", *Trends in Genetics*, Jun. 1998;14(6):248-250.
Dudek et al., 1997, *C. J. Biol. Chem.*, 272:31785-31792.
Emery et al., 1995, Strategies for humanizing antibodies, in: *Antibody Engineering*, $2^{nd}$ ed., Ed. Borrebaeck CAK, pp. 159-183, Oxford University Press, Oxford.
Fell et al., 1989, *Proc. Natl. Acad. Sci. USA*, 86:8507-8511.
Fratantoni et al., 1975, *Blood*, 45:395.
Gennaro et al, *Remington's Pharmaceutical Sciences*, Mack Publishing Co., Easton, PA, 1985; cover page, title page, copyright page and table of contents only; 5 pgs.
Gerhardt et al., *Methods for General and Molecular Bacteriology*, American Society for Microbiology, Washington, DC, 1994; title page and table of contents only; 2 pgs.
Greinacher et al., 1992, *Thromb. Haemost.*, 67:545.
Greinacher et al., 1994, *Thromb. Haemost.*, 71:247.
Greinacher et al., 1995, *Thrombosis and Haemostasis*, 74:886-892.
Gu et al., 1997, *Thrombosis and Hematocyst*, 77(4):755-759.
Harlow et al., *Antibodies: A Laboratory Manual*, Cold Spring Harbor Laboratory, New York, NY, 1988; cover page, copyright page and pp. 479-504.
Hattori et al., 1990, *Proc. Natl. Acad. Sci.*, 87:2364-2368.
Herbert et al., 1998, *Thromb. Haemost.*, 80:326.
Hulett et al., "Molecular Basis of Fc Receptor Function", *Adv. Immunol*, 1994;57:1-127.
Horsewood et al., 1996, *Br. J. Haematol.*, 95:161.
Huston et al., 1988, *Proc. Natl. Acad. Sci USA*, 85:5879-5883.
Jaffe et al., 1973, *J. Clin. Invest.*, 52:2745.
Jones et al., 1986, *Nature*, 321:522-525.
Kabat et al., Sequences of Proteins of Immunological Interest, $5^{th}$ ed., National Institutes of Health, Bethesda, MD, 1991; cover page and table of contents only; 10 pgs.
Karlin et al., "Methods for assessing the statistical significance of molecular sequence features by using general scoring schemes", *Proc. Natl. Acad. Sci. USA*, Mar. 1990;87(6):2264-2268.
Karlin et al., 1993, *Proc. Natl. Acad. Sci USA*, 90:5873-5877.
Kelton et al., 1988, *Blood*, 72:925.
Kelton et al., "Immunoglobulin G from patients with heparin-induced thrombocytopenia binds to a complex of heparin and platelet factor 4", *Blood*, 1994;83:3232-3239.
Knight et al., 1995, *Mol. Immunol.*, 32:1271-1281.
Konkle et al., "Heparin-induced thrombocytopenia: bovine versus porcine heparin in cardiopulmonary bypass surgery", *Ann. Thorac. Surg.*, Jun. 2001;71(6):1920-1924.
Lane et al., "High Efficiency Fusion Procedure for Producing Monoclonal Antibodies against Weak Immunogens", *Methods in Enzymology*, 1986;121:183-192.
Lee et al., 1996, *Br. J. Haematol.*, 95:724-731.
Lee et al., 1998, *Thromb. Haemost.*, 79:50.
Li et al., "Defining a second epitope for heparin-induced thrombocytopenia/thrombosis antibodies using KKO, a murine HIT-like monoclonal antibody", *Blood*, Feb. 15, 2002;99(4):1230-1236.
Ma et al., "A murine model for heparin-induced thrombocytopenia (HIT)", *Blood*, Nov. 15, 1999;94(10).
Marks et al., 1991, *J. Mol. Biol.*, 222:581-597.
Mayo et al., 1995, *Biochem. J.*, 312:357.
McCrae et al., 1990, *J. Immunol.*, 144:3920.
Morrison et al., 1984, *Proc. Natl. Acad. Sci. USA*, 81:6851-6855.
Newman et al., 1998, *Thrombosis and Haemostasis*, 80:292-297.
Ngo et al., "Computational Complexity, Protein Structure Prediction, and the Levinthal Paradox" *The Protein Folding Problem and Tertiary Structure Prediction*, Boston, MA, 1994; cover page, copyright page, table of contents and pp. 492-495.
Park et al., 1990, *Blood*,75:1290.
Polgar et al., 1998, *Blood*, 91:549-554.
Rauova et al., "Ultralarge complexes of PF4 and heparin are central to the pathogenesis of heparin-induced thrombocytopenia", *Blood*, Jan. 1, 2005;105(1): 131-138, Epub Aug. 10, 2004.
Reilly et al., "Heparin-induced thrombocytopenia/thrombosis in a transgenic mouse model requires human platelet factor 4 and platelet activation through FcgammaRIIA", *Blood*, Oct. 15, 2001;98(8):2442-2447.
Riechmann et al., 1988, *Nature*, 332:323-327.
Rosenfeld, et al., 1987, *J. Immunol.*, 138:2569.
Saggin, et al., "Neutralization of the antiheparin activity of platelet factor 4 by a monoclonal antibody", *Thrombosis and Haemostasis*, Jan. 23, 1992;67(1):137-143.
Sambrook et al., *Molecular Cloning: A Laboratory Manual*, Cold Spring Harbor Laboratory Press, New York, NY, 1989; cover page, copyright page and table of contents only; 30 pgs.
Schmitt et al., 1993, *Am. J. Med. Sci.*, 305:208.
Sheridan et al., 1986, *Blood*, 67:27-30.
Siegel et al., "Expression and characterization of recombinant anti-Rh(D) antibodies on filamentous phage: a model system for isolating human red blood cell antibodies by repertoire cloning", *Blood*, 1994;83:2334-2344.
Skolnick et al., "From genes to protein structure and function: novel applications of computational approaches in the genomic era", *Trends in Biotech.*, Jan. 2000;18(1):34-39.
Smith et al., "The challenges of genome sequence annotation or 'the devil is in the details'", *Nature Biotechnol.*, Nov. 1997;15(12):1222-1223.
Stern et al, 1985, *J. Clin. Invest.*, 75:272.
Stewart et al., 1995, *British J. Haematol.*, 91:173-177.
Suh et al., 1997, *Am. J. Hematol.*, 54:196.
Suh et al., 1998, *Blood*, 91(3):916-922.
Tannenbaum et al., 1986, *J. Immunol.*, 137:1532.
Tomer, 1997, *Br. J. Haematol.*, 98:648-656.
Tomlinson, 1988, *Trends in Pharm. Sci.*, 9:159-162.
Trossaert et al., 1998, *Br. J. Haematol.*, 101:653.
Tuszynski et al., "Thrombospondin promotes platelet aggregation", *Blood*, Jul. 1988;72(1):109-115.
Visentin et al., 1994, *J. Clin. Invest.*, 93:81-88.
Visentin et al., 1996, *J. Lab. Clin. Med.*, 128:376.
Warkentin et al., 1996, *Am. J. Med.*, 101:502-507.
Wells, "Additivity of mutational effects in proteins", *Biochem*, Sep. 18, 1990;29(37):8509-8517.
Wright et al., 1992, *Critical Rev. in Immunol.*, 12(3,4):125-168.
Ziporen et al., "Defining an antigenic epitope on platelet factor 4 associated with heparin-induced thrombocytopenia", *Blood*, Nov. 1, 1998;92(9):3250-3259.

\* cited by examiner

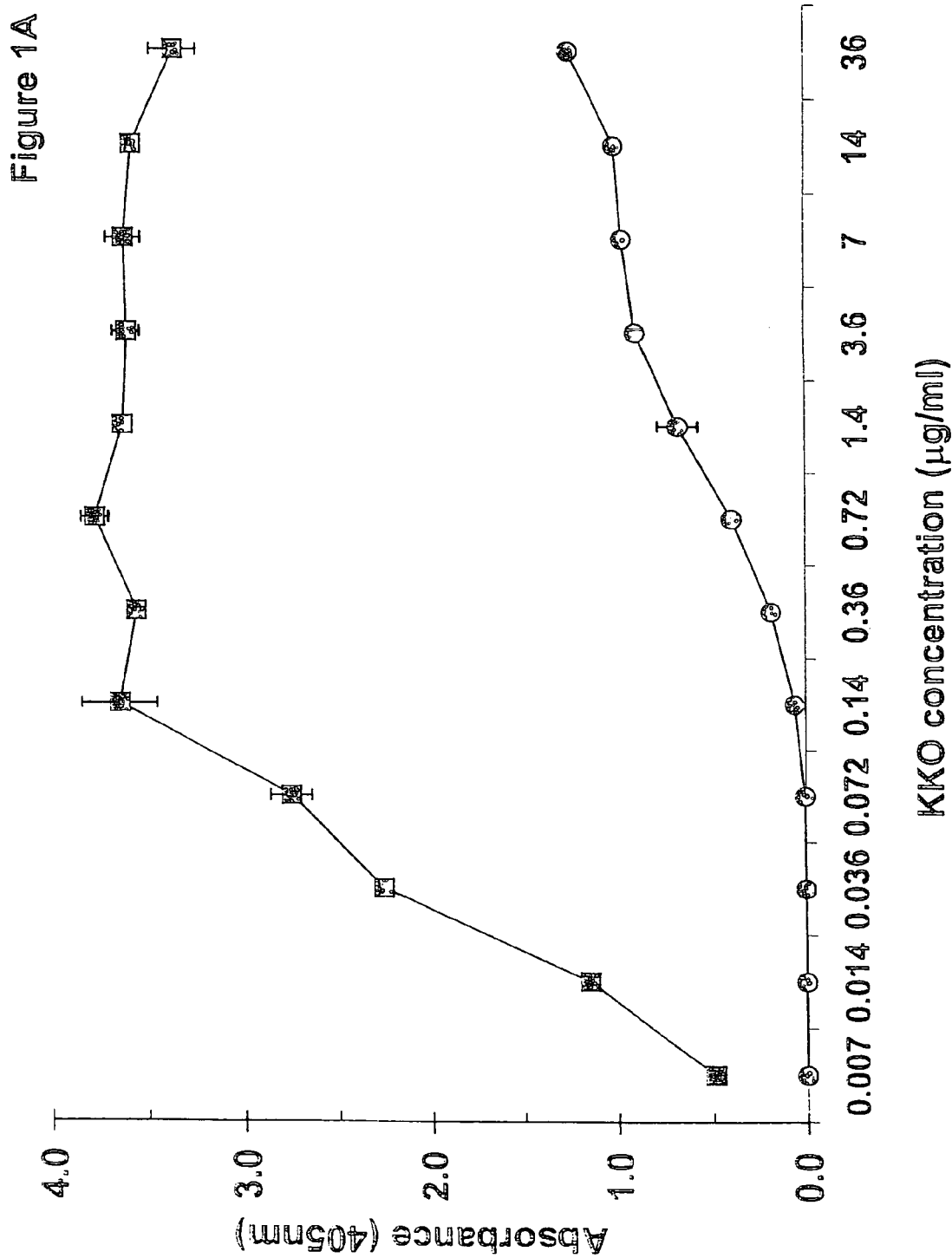

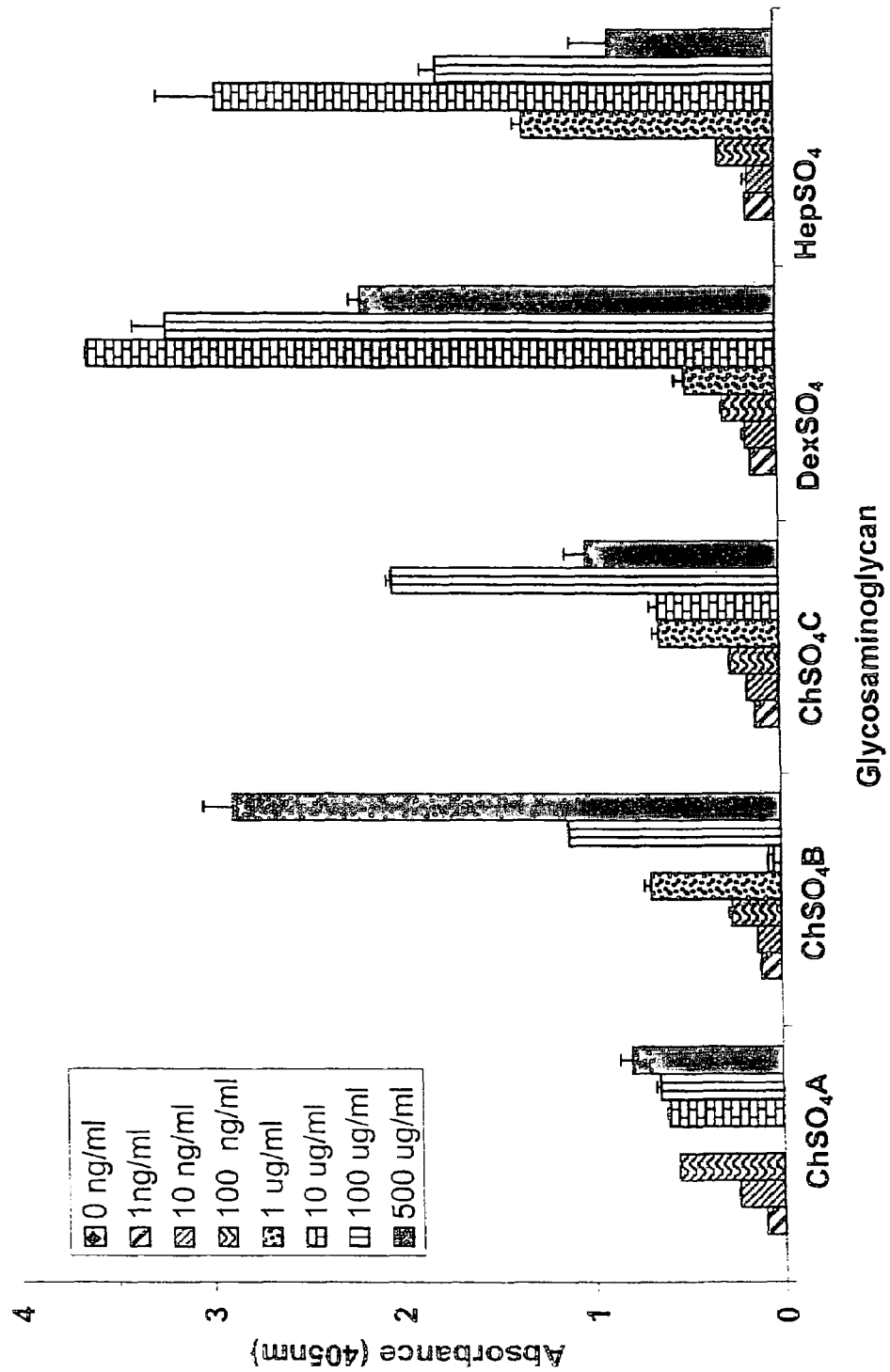

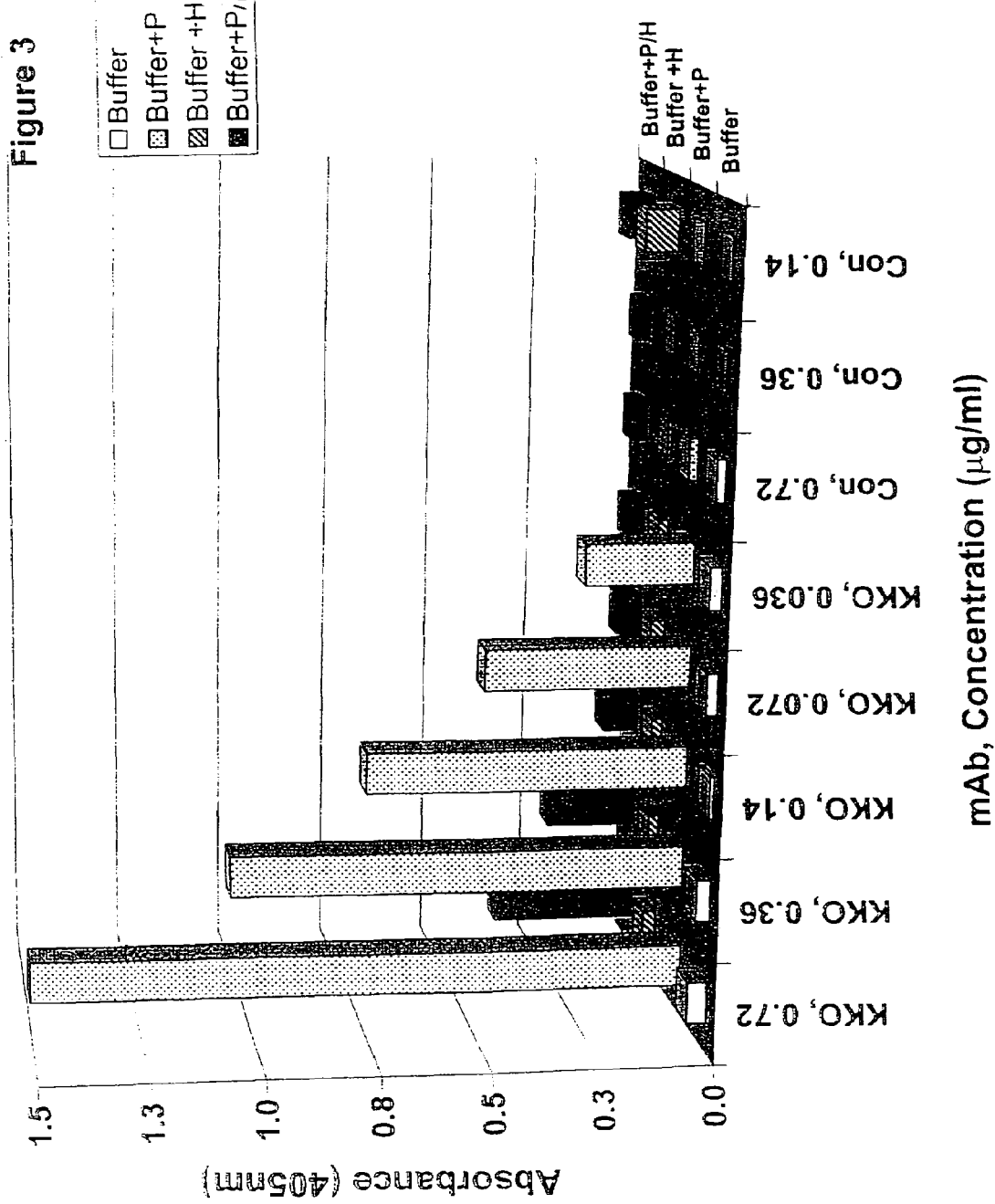

EVQLQQSGAELVKPGASVKLSCKASGYTFTNYFIYWVKQRPGQGLEWIGEINPR
NGDTDFNEKFESRATLTVDKSSSTAYMQLSSLTSEDSAIYYCTRSPYGNNYGFTY
WGQGTLVTVSA

FIGURE 7B

AELDIQMIQSQKFMSTSVGDRVTVTCKASQNVGTNVAWYQQKPGQSPNALIYS
ASYRYSGVPDRFTGSGSGTDFTLTITNVQSEDLADYFCQQYNSYPLTFGTGTKLEI
K

FIGURE 7C

GAGGTTCAGCTGCAGCAGTCTGGGGCTGAACTGGTGAAGCCTGGGGCTTCAG
TGAAGTTGTCCTGTAAGGCTTCTGGCTACACCTTCACCAATTACTTTATATAC
TGGGTGAAGCAGAGGCCTGGACAAGGCCTTGAGTGGATTGGAGAGATTAATC
CTAGAAATGGTGATACTGACTTCAATGAGAAGTTCGAGAGCAGGGCCACACT
GACTGTAGACAAATCCTCCAGCACGGCATACATGCAACTCAGCAGCCTGACA
TCTGAGGACTCTGCGATCTATTACTGTACAAGATCCCCCTACGGTAATAACTA
CGGGTTTACTTACTGGGGCCAAGGGACTCTGGTCACTGTCTCTGCA

FIGURE 7D

GCCGAGCTCGATATTCAGATGATTCAGTCTCAAAAATTCATGTCCACATCAGT
AGGAGACAGGGTCACCGTCACCTGCAAGGCCAGTCAGAATGTGGGTACTAAT
GTAGCCTGGTATCAACAGAAACCAGGGCAATCTCCTAATGCACTGATTTACT
CGGCATCCTACCGGTACAGTGGAGTCCCTGATCGCTTCACAGGCAGTGGATC
TGGGACAGATTTCACTCTCACCATCACCAATGTGCAGTCTGAAGACTTGGCA
GACTATTTCTGTCAGCAATATAACAGCTATCCTCTCACATTCGGTACTGGCAC
CAAACTGGAAATCAAA

Figure 7

COMPOSITIONS AND METHODS USEFUL FOR THE DIAGNOSIS AND TREATMENT OF HEPARIN INDUCED THROMBOCYTOPENIA/THROMBOSIS

CROSS-REFERENCE TO RELATED APPLICATIONS

This application is a continuation of U.S. patent application Ser. No. 09/615,872, filed Jul. 13, 2000, which claims the benefit of U.S. provisional patent application 60/143,536, filed on Jul. 13, 1999.

STATEMENT REGARDING FEDERALLY SUPPORTED RESEARCH AND DEVELOPMENT

This invention was supported in part by U.S. Government funds (NHLBI/NIH Grant No. 2RO1 HL 35246, NIH/NCI Grant No. P20RR11830 and NIH Grant No. KO8 HL04009), and the U.S. Government may therefore have certain rights in the invention.

BACKGROUND OF THE INVENTION

Heparin-induced thrombocytopenia (HIT) is a drug-induced blood disorder that affects 1-5% of patients who are treated with the blood-thinning drug heparin (Chong, 1995, British Journal of Haematology, 89(3):431-9). Patients who develop HIT are at risk for developing life-threatening clots in the heart, the brain, the extremities or the lungs (Arepally et al., 1998, Clinical Reviews in Allergy and Immunology, 16:1-11). HIT is caused by antibodies which bind specifically with a complex comprising the protein Platelet Factor 4 (PF4) and heparin, a sugar compound classified as a glycosaminoglycan (Amiral et al., 1992, Thrombosis & Haemostasis, 68(1):95-6). Antibodies directed against the PF4/heparin complex can be demonstrated in the blood of patients with HIT, and are associated with the clotting problems seen in these patients. Antibodies to the PF4/heparin complex which have been isolated from humans (Suh et al. 1998, Blood, 91(3):916-22) and mice (Blank et al., 1997, Clin. Exp. Immunol. 108(2): 333-9) are polyclonal and heterogeneous since they are derived from the natural polyclonal immune response of an organism to an antigen.

Although autoantibodies against the PF4/heparin complex can be identified in the plasma of more than 90% of patients who develop the clinical syndrome of HIT (Arepally et al., 1995, Am. J. Clin. Pathol. 104:648), these antibodies can also be demonstrated in a significant proportion (15-70%) of asymptomatic patients repetitively exposed to heparin (Amiral et al., 1996, Am. J. Hematol. 52:90; Visentin et al., 1996, J. Lab. Clin. Med. 128:376; Trossaert et al., 1998, Br. J. Haematol. 101:653; Bauer et al., 1997, Circulation 95:1242). The reason why only a subset of immunized patients develop symptomatic disease is unknown (Schmitt et al., 1993. Am. J. Med. Sci. 305:208; Warkentin et al., 1996, Am. J. Med. 101: 502; Sheridan et al., 1986, Blood 67:27). The molecular basis for a pathogenic role of antibodies to the PF4/heparin complex has been difficult to establish, since the antibodies are polyclonal and polyspecific.

Heterogeneity in disease expression may, in part, reflect differences in co-morbid factors that predispose to thrombosis, such as atherosclerosis, surgery and vascular trauma (Boshkov et al., 1993, Br. J. Haematol. 84:322; Lee et al., 1998, Thromb. Haemost. 79:50). Others have implicated differences in antibody titer (Suh et al., 1997, Am. J. Hematol. 54:196), affinity (Suh et al., 1998, Blood 91:916), isotype (Amiral et al., 1996, Br. J. Haematol. 92:954), subclass (Suh et al., 1997, Am. J. Hematol. 54:196; Arepally et al., 1997, Blood 89:370), and platelet Fc receptor polymorphism (Fc-γRIIA-H/$R^{131}$) (Carlsson et al., 1998, Blood 92:1526) in affected individuals. However, it is clear that such serologic or clinical differences do not permit unambiguous segregation of asymptomatic patients with anti-PF4/heparin complex antibodies from those who develop thrombocytopenia and those who develop thrombocytopenia and thrombosis (Arepally et al., 1997, Blood 89:370; Bachelot-Loza et al., 1998, Thromb. Haemost. 79:523; Herbert et al., 1998, Thromb. Haemost. 80:326).

An additional explanation for the observed heterogeneity in disease expression may lie in the heterogeneity of anti-PF4/heparin complex antibodies themselves. Because PF4 modulates heparin-dependent anti-thrombin (Stern et al., 1985, J. Clin. Invest. 75:272) and protein C co-factor activities (i.e., pro- and anti-coagulant activities {Dudek et al., 1997, C. J. Biol Chem 272:31785}), the effects on these or other coagulant functions of PF4 by antibodies to the PF4/heparin complex remains to be elucidated. Anti-PF4/heparin complex antibodies differ in their antigen specificities, although the responsible determinants have not been clearly delineated (Suh et al., 1997, Am. J. Hematol. 54:196; Ziporen et al., 1998, Blood 92: 3250; Amiral et al., 1996, Blood 88:410; Horsewood et al., 1996, Br. J. Haematol. 95:161). However, the polyclonal nature of the naturally occurring immune response complicates any attempt to determine whether a subset of anti-PF4 antibodies are responsible for thrombosis.

Because of the limited and heterogeneous supply of antibodies from patients with heparin induced thrombocytopenia and/or thrombosis (HIT/HITT), it has been difficult to characterize the pathogenic properties of antibodies to the PF4/heparin complex. Furthermore, in diagnosing HIT/HITT, antibodies to the PF4/heparin complex are needed as a positive control. Until now, tests have relied on the availability of antibodies from patients with HIT/HITT as a "positive control". Thus, there remains a need in the art for compositions and methods which are useful in the diagnosis and treatment of HIT/HITT, or in the elucidation of the role of antibodies to the PF4/heparin complex in the development of HIT/HITT. The present invention meets this need.

BRIEF SUMMARY OF THE INVENTION

The invention includes a composition comprising a monoclonal antibody which is capable of binding specifically with a PF4/heparin complex, wherein the antibody preferentially binds with the PF4/heparin complex relative to the binding of the antibody with either PF4 or heparin alone.

In one embodiment, the monoclonal antibody is capable of binding specifically with a glycosaminoglycan which is not heparin.

In another embodiment, the monoclonal antibody is capable of activating platelets in the presence of PF4 and heparin.

In one aspect, the antibody comprises a heavy chain polypeptide having an amino acid sequence which shares at least about 80% homology with SEQ ID NO:1 and a light chain polypeptide having an amino acid sequence which shares at least about 80% homology with SEQ ID NO:2.

In another aspect, the antibody is a murine monoclonal antibody (KKO) which comprises the heavy chain polypeptide of SEQ ID NO:1 and the light chain polypeptide of SEQ ID NO:2.

In one embodiment, the antibody is a humanized antibody.

The invention also includes a composition comprising an isolated nucleic acid, wherein the isolated nucleic acid encodes an antibody which is capable of binding specifically with a PF4/heparin complex, wherein the antibody preferentially binds with the PF4/heparin complex relative to the binding of the antibody with either PF4 or heparin alone the isolated nucleic acid comprising a nucleotide sequence which shares at least about 80% homology with SEQ ID NO:3 and a nucleotide sequence which shares at least about 80% homology with SEQ ID NO:4.

In one embodiment, the isolated nucleic acid comprises the nucleotide sequences of SEQ ID NO:3 and SEQ ID NO:4.

In another embodiment, the isolated nucleic acid encodes a humanized monoclonal antibody.

In one aspect, the composition is in the form of a pharmaceutical composition.

The invention also includes a method of making a humanized monoclonal antibody which is capable of binding specifically with a PF4/heparin complex, wherein the antibody preferentially binds with the PF4/heparin complex relative to the binding of the antibody with either PF4 or heparin alone. The method comprises a) obtaining a monoclonal antibody which is capable of binding specifically with a PF4/heparin complex, wherein the antibody preferentially binds with the PF4/heparin complex relative to the binding of the antibody with either PF4 or heparin alone; b) humanizing the antibody in a), whereby a humanized monoclonal antibody is made.

In one aspect, the monoclonal antibody in a) comprises a heavy chain polypeptide having an amino acid sequence which shares at least about 80% homology with SEQ ID NO:1 and a light chain polypeptide having an amino acid sequence which shares at least about 80% homology with SEQ ID NO:2.

In another aspect, the monoclonal antibody in a) is a murine monoclonal antibody (KKO) which comprises the heavy chain polypeptide of SEQ ID NO:1 and the light chain polypeptide of SEQ ID NO:2.

The invention also includes a method of diagnosing HIT/HITT in a mammal. The method comprises a) assessing the level of a polyclonal antibody in a sample of a bodily fluid or tissue obtained from the mammal, wherein the polyclonal antibody binds specifically with a PF4/heparin complex and preferentially binds with the PF4/heparin complex relative to the binding of the polyclonal antibody with either PF4 or heparin alone; b) comparing the level of the polyclonal antibody in the sample with the level of a monoclonal antibody which is specific for the PF4/heparin complex in a positive control sample for HIT/HITT, wherein the monoclonal antibody preferentially binds with the PF4/heparin complex relative to the binding of the monoclonal antibody with either PF4 or heparin alone; and c) determining from a) and b) whether the level of the polyclonal antibody in the sample is statistically similar to the level of the monoclonal antibody in the positive control sample, wherein when the level of the polyclonal antibody is statistically similar to the level of the monoclonal antibody in the positive control sample, then HIT/HITT is diagnosed in the mammal.

In one aspect, the mammal is a human.

In another aspect, the monoclonal antibody is a murine monoclonal antibody comprising a heavy chain polypeptide of SEQ ID NO:1 and a light chain polypeptide of SEQ ID NO:2.

In one embodiment, the level of the polyclonal antibody and the level of the monoclonal antibody are each assessed using an assay independently selected from the group consisting of an ELISA assay, a Western blotting assay, a serotonin release assay, a platelet aggregation assay, a lumi-aggregometry assay and a flow cytometry assay.

The invention also includes a method of assessing the level of a polyclonal antibody in a bodily fluid or tissue sample obtained from a mammal, wherein the polyclonal antibody binds specifically with a PF4/heparin complex and preferentially binds with the PF4/heparin complex relative to the binding of the polyclonal antibody with either PF4 or heparin alone. The method comprises a) assessing the level of the polyclonal antibody in the bodily fluid or tissue sample obtained from the mammal; b) comparing the level of the polyclonal antibody in the sample with the level of a monoclonal antibody which is specific for the PF4/heparin complex in a reference standard which comprises the monoclonal antibody, wherein the monoclonal antibody preferentially binds with the PF4/heparin complex relative to the binding of the monoclonal antibody with either PF4 or heparin alone; and c) determining from a) and b) the level of the polyclonal antibody in the sample, whereby the level of the polyclonal antibody in the sample is assessed.

The invention also includes a method of identifying a functional element of an antibody, wherein the functional element participates in the pathogenesis of HIT/HITT in a mammal. The method comprises a) preparing one or more deletion or substitution mutants of a monoclonal antibody which bind specifically with a PF4/heparin complex and which preferentially bind with the PF4/heparin complex relative to the binding of either PF4 or heparin alone, wherein the one or more deletion or substitution mutants lack a portion of the amino acid sequence of the Fab region of the monoclonal antibody; b) assessing the ability of each of the deletion or substitution mutants to bind specifically with a PF4/heparin complex and to preferentially bind with the PF4/heparin complex relative to the binding of the deletion or substitution mutant with either PF4 or heparin alone; c) identifying, from b) one or more of the deletion or substitution mutants which does not preferentially bind with the PF4/heparin complex relative to the binding of the deletion or substitution mutant with either PF4 or heparin alone; and d) determining from c) and a) the corresponding deleted portion of the amino acid sequence of the monoclonal antibody which participates in the preferential binding with the PF4/heparin complex, whereby a functional element of the monoclonal antibody which participates in the pathogenesis of HIT/HITT is identified.

In one aspect, the monoclonal antibody comprises a heavy chain polypeptide having an amino acid sequence which shares at least about 80% homology with SEQ ID NO:1 and a light chain polypeptide having an amino acid sequence which shares at least about 80% homology with SEQ ID NO:2.

The invention also includes a method of treating HIT/HITT in a mammal. The method comprises a) administering to the mammal a composition comprising a monoclonal antibody or a functional element thereof which binds specifically with a PF4/heparin complex and which preferentially binds with the PF4/heparin complex relative to the binding of the monoclonal antibody with either PF4 or heparin alone, wherein the monoclonal antibody or the functional element thereof is present in the composition in an amount effective to competitively inhibit the specific binding of a polyclonal antibody in the mammal to the PF4/heparin complex; and b) inhibiting the specific binding of the polyclonal antibody in the mammal with the PF4/heparin complex, thereby treating HIT/HITT in the mammal.

In one aspect, the mammal is a human.

In another aspect, the monoclonal antibody comprises a heavy chain polypeptide having an amino acid sequence which shares at least about 80% homology with SEQ ID NO:1 and a light chain polypeptide having an amino acid sequence which shares at least about 80% homology with SEQ ID NO:2.

In a further aspect, the monoclonal antibody is a humanized antibody

In one embodiment, the monoclonal antibody is a murine monoclonal antibody comprising a heavy chain polypeptide having SEQ ID NO:1 and a light chain polypeptide having SEQ ID NO:2.

The invention also includes a method of identifying a compound which is a modulator of the specific binding of an antibody to a PF4/heparin complex. The method comprises a) contacting the compound with the antibody and the PF4/heparin complex; and b) assessing the effect of the compound upon the specific binding of the antibody to the PF4/heparin complex, wherein a higher or lower level of specific binding of the antibody to the PF4/heparin complex in the presence of the compound compared with the level of specific binding of the antibody to the PF4/heparin complex in the absence of the compound is an indication that the compound is a modulator of the specific binding of an antibody to a PF4/heparin complex.

In one aspect, the antibody is a monoclonal antibody.

In another aspect, the antibody is a polyclonal antibody.

In one embodiment, the antibody is a murine monoclonal antibody comprising a heavy chain polypeptide which shares at least about 80% homology with SEQ ID NO:1 and a light chain polypeptide which shares at least about 80% homology with SEQ ID NO:2.

In another embodiment, the antibody is a murine monoclonal antibody comprising a heavy chain polypeptide which is SEQ ID NO:1 and a light chain polypeptide which is SEQ ID NO:2.

The invention also includes a kit for diagnosing HIT/HITT in a mammal. The kit comprises a) a positive control solution comprising a monoclonal antibody or a functional element thereof which binds specifically with a PF4/heparin complex, wherein the monoclonal antibody or the functional element thereof preferentially binds with the PF4/heparin complex relative to the binding of the monoclonal antibody or the functional element thereof with either PF4 or heparin alone; and b) an instructional material describing the use of the positive control solution for diagnosing HIT/HITT in a mammal.

In one aspect, the monoclonal antibody comprises a heavy chain polypeptide having an amino acid sequence which shares at least about 80% homology with SEQ ID NO:1 and a light chain polypeptide having an amino acid sequence which shares at least about 80% homology with SEQ ID NO:2.

In another aspect, the monoclonal antibody is a murine monoclonal antibody (KKO) comprising a heavy chain polypeptide of SEQ ID NO:1 and a light chain polypeptide of SEQ ID NO:2.

In a further aspect, the monoclonal antibody is a humanized antibody.

The invention also includes a kit for use in treating a mammal afflicted with HIT/HITT. The kit comprises a) a composition comprising a monoclonal antibody or a functional element thereof which binds specifically with a PF4/heparin complex, wherein the monoclonal antibody or the functional element thereof preferentially binds with the PF4/heparin complex relative to the binding of the monoclonal antibody or the functional element thereof with either PF4 or heparin alone, wherein the monoclonal antibody or the functional element thereof is present in the composition in an amount effective to competitively inhibit the specific binding of a polyclonal antibody in the mammal to the PF4/heparin complex; and b) an instructional material describing the use of the composition for the treatment of HIT/HITT in the mammal.

In one aspect, the monoclonal antibody is a humanized antibody.

In another aspect, the monoclonal antibody comprises a heavy chain polypeptide having an amino acid sequence which shares at least about 80% homology with SEQ ID NO:1 and a light chain polypeptide having an amino acid sequence which shares at least about 80% homology with SEQ ID NO:2.

In a further aspect, the monoclonal antibody is a murine monoclonal antibody (KKO) comprising a heavy chain polypeptide of SEQ ID NO:1 and a light chain polypeptide of SEQ ID NO:2.

BRIEF DESCRIPTION OF THE DRAWINGS

The foregoing summary, as well as the following detailed description of the invention, will be better understood when read in conjunction with the appended drawings.

FIG. 1, comprising FIGS. 1A-1C, is a series of graphs depicting the binding of murine monoclonal antibody clones KKO and RTO to PF4. FIG. 1A depicts the binding of KKO to microtiter wells coated with hPF4 (line indicated by circles) or with a hPF4/heparin complex (line indicated by squares). FIG. 1B depicts the binding of RTO to wells coated with hPF4 (line indicated by squares) or with a hPF4/heparin complex (line indicated with circles). FIG. 1C depicts the heparin dependence of KKO as measured by ELISA using wells coated with a fixed concentration of hPF4 and varying concentrations of heparin. The data presented represent the mean±1 standard deviation of duplicate wells and are representative of three independent measurements.

FIG. 2 is a graph depicting the reactivity of the murine monoclonal antibody KKO to hPF4/glycosaminoglycan complexes. The binding of KKO with PF4 in a complex with glycosaminoglycans (GAGs) was assayed using an ELISA method described herein. Sample wells were coated with a fixed concentration of hPF4 (10 micrograms per milliliter) and the indicated concentration of either chondroitin sulfate A ($ChSO_4A$), chondroitin sulfate B ($ChSO_4B$), chondroitin sulfate C ($ChSO_4C$), dextran sulfate ($DexSO_4$) and heparan sulfate ($HepSO_4$). The data presented represent the mean±1 standard deviation of duplicate wells and are representative of two independent measurements.

FIG. 3 is a graph depicting the binding of KKO at various concentrations to human umbilical vein epithelial cells (HUVECs). The reactivity of KKO or an isotype control antibody (Con) to microtiter plates coated with HUVECs in the presence of either buffer or buffer containing hPF4(P), heparin (H), or hPF4/heparin complex (P/H). The data presented represent the mean of triplicate measurements and are representative of two independent measurements.

FIG. 5, comprising FIG. 5A depicts the binding of KKO to single amino acid hPF4 mutants complexed to heparin as measured by ELISA. FIG. 5B depicts the results of competition studies of KKO binding to the hPF4/heparin complex using HIT plasma at increasing concentrations with the results expressed as percent of $A_{405}$ seen when no HIT plasma was included. The competition studies shown in black represent 4 different HIT patients "insensitive" to 3rd-domain mutations of hPF4, while the competition studies shown in gray represent HIT patients "sensitive" to 3rd-domain mutations of hPF4. The 50% level of reduction in $A_{405}$ is indicated as a dashed line. Results are the mean±1 standard deviation of three separate experiments performed in duplicate.

FIG. 6, comprising FIGS. 6A and 6B, is a pair of schematics depicting a comparison of the amino acid sequence of the murine monoclonal antibodies KKO and RTO. FIG. 6A depicts a comparison of the amino acid sequence of the heavy chain polypeptides of the antibodies. The upper panel o FIG. 6A is KKO heavy chain (SEQ ID NO:11) and the lower panel is RTO heavy chain (SEQ ID NO:12). FIG. 6B depicts a comparison of the amino acid sequence of the light chain polypeptides. The upper panel of FIG. 6B is KKO light chain (SEQ ID NO: 13) and the lower panel is RTO light chain (SEQ ID NO: 14). Assigned variable region gene families and J-gene segments are as indicated. Amino acid residue numbering and framework (FR) and complementarity-determining region (CDR) designations are per Kabat et al., 1991 ("Sequences of Proteins of Immunological Interest", 5$^{th}$ ed. Bethesda, National Institutes of Health). ">" indicates an amino acid residue encoded by a PCR primer.

FIG. 7, comprising FIGS. 7A-7D, is a listing of the amino acid and nucleotide sequences SEQ ID NOs: 1-4. FIG. 7A (SEQ ID NO:1) is the amino acid sequence of the heavy chain polypeptide of the murine monoclonal antibody KKO. FIG. 7B (SEQ ID NO:2) is the amino acid sequence of the light chain polypeptide of the murine monoclonal antibody KKO. FIG. 7C (SEQ ID NO:3) is the nucleotide sequence of an isolated nucleic acid which encodes the heavy chain polypeptide of KKO. FIG. 7D (SEQ ID NO:4) is the nucleotide sequence of an isolated nucleic acid which encodes the light chain polypeptide of KKO.

DETAILED DESCRIPTION OF THE INVENTION

Figure 1B:
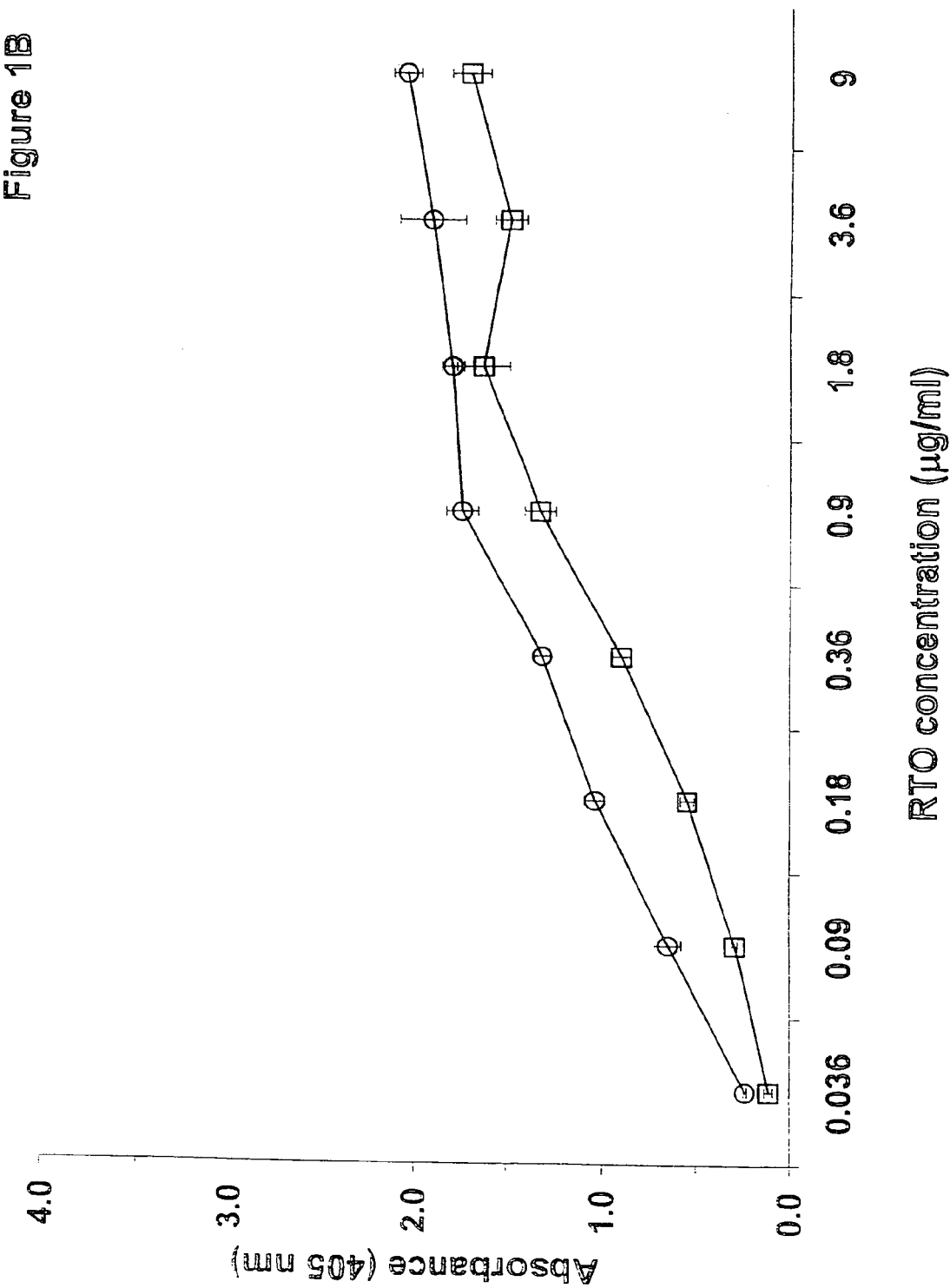

The present invention includes compositions, kits and methods pertaining to a monoclonal antibody which binds specifically with a PF4/heparin complex. The antibody is exemplified herein by a murine monoclonal antibody which exhibits several features which are critically similar to key features of the polyclonal human antibodies which participate in the pathogenesis of heparin-induced thrombocytopenia and/or thrombosis (HIT/HITT). These features include preferential binding to a PF4/heparin complex relative to binding of the antibodies with either PF4 or heparin alone, specific binding of the antibody to complexes of PF4 with other sulfated glycosaminoglycans (GAGs) besides heparin, and platelet activation in the presence of the PF4/heparin complex. The exemplified murine monoclonal antibody disclosed herein is the first known monoclonal antibody which preferentially binds the PF4/heparin complex relative to either PF4 or heparin alone. Because this monoclonal antibody shares key serologic and functional properties with naturally occurring human polyclonal antibodies specific for the PF4/heparin complex found in patients with HIT/HITT, the monoclonal antibody is useful in methods for the diagnosis, treatment, and understanding of the pathogenesis of HIT/HITT in a mammal. Thus, the invention should not be construed as being limited solely to the antibody exemplified herein, but rather should be construed to include derivatives of this antibody, including humanized versions thereof as disclosed herein.

Definitions

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

As used herein, the term "pathogenesis of HIT/HITT" means one or more of the development of a symptom of HIT/HITT, the development of an underlying physiological or molecular disorder which contributes to HIT/HITT, or the development of a pathological or deleterious physiological consequence of HIT/HITT in the mammal.

As used herein, the term "bind specifically with" or "specific binding" in the context of an antibody means to bind substantially to an antigen, without binding substantially to other molecules which are present with the antigen.

As used herein, the term "preferentially binds" or to "bind preferentially" means, in the context of an antibody, the binding of an antibody with a complex of more than one molecule with substantially greater affinity than the binding of the antibody with either of the molecules which comprise the complex alone.

As used herein, the phrase "to treat HIT/HITT" or "treating HIT/HITT" in a mammal means one or more of alleviating a symptom of, correcting an underlying molecular or physiological disorder of, or reducing the frequency or seventy of a pathological or deleterious physiological consequence of HIT/HITT in the mammal. By way of example, and not by limitation, the deleterious physiological consequences of HIT/HITT include stroke, myocardial infarction, arterial and venous thrombi, vascular gangrene and skin necrosis. Without wishing to be bound by any one theory, it is suspected that a composition of the invention could, by way of example and not by limitation, effect treatment of HIT/HITT by one or more of blocking antigenic sites on a PF4/heparin complex which are recognized by human polyclonal antibodies, binding Fc receptors and preventing activation of platelets or endothelial cells, and creating an anti-idiotype response which could neutralize human polyclonal antibodies.

As used herein, the term "antibody" means an immunoglobulin molecule which is able to bind specifically to a specific epitope on an antigen. Antibodies can be intact immunoglobulins derived from natural sources or from recombinant sources and can be immunoreactive portions (i.e. functional elements) of intact immunoglobulins. The antibodies in the compositions and methods of the present invention may exist in a variety of forms including, for example, polyclonal antibodies, monoclonal antibodies, Fv, Fab and F(ab)$_2$, as well as single chain antibodies and humanized antibodies (Harlow et al., 1988, Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

As used herein, the term "isolated polypeptide" refers to a polypeptide segment or fragment which has been separated from sequences which flank it in a naturally occurring state, e.g., a polypeptide fragment which has been removed from the sequences which are normally adjacent to the fragment, e.g., the sequences adjacent to the fragment in a protein in which it naturally occurs. The term also applies to a polypeptide which has been substantially purified from other components which naturally accompany the polypeptide, e.g., proteins, RNA or DNA which naturally accompany it in the cell. The term therefore includes, for example, a recombinant polypeptide which is encoded by a nucleic acid incorporated into a vector, into an autonomously replicating plasmid or virus, or into the genomic DNA of a prokaryote or eukaryote, or which exists as a separate molecule (e.g, as a cDNA or a genomic or cDNA fragment produced by PCR or restriction enzyme digestion) independent of other sequences. It also includes a recombinant polypeptide which is part of a hybrid polypeptide comprising additional amino acids. An isolated polypeptide of the invention is exemplified by the isolated polypeptides of SEQ ID NO:1 and SEQ ID NO:2 (the heavy and light chain polypeptides, respectively, of the murine monoclonal antibody KKO described herein).

As used herein, the term "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g, as a cDNA or a genomic or cDNA fragment produced by PCR or restriction enzyme digestion) independent of other sequences. It also includes a recombinant DNA which is part of a hybrid gene encoding additional polypeptide sequence.

As used herein, the term "recombinant polynucleotide" refers to a polynucleotide having sequences that are not naturally joined together. An amplified or assembled recombinant polynucleotide may be included in a suitable vector, and the vector can be used to transform a suitable host cell. A recombinant polynucleotide may serve a non-coding function (e.g., promoter, origin of replication, ribosome-binding site, etc.) as well. A host cell that comprises a recombinant polynucleotide is referred to as a "recombinant host cell." A gene which is expressed in a recombinant host cell wherein the gene comprises a recombinant polynucleotide, expresses a "recombinant polypeptide."

As used herein, the term "recombinant polypeptide" means a polypeptide which is produced upon expression of a recombinant polynucleotide.

As used herein, the term "polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer.

The term "protein" typically refers to large polypeptides.

The term "peptide" typically refers to short polypeptides.

Conventional notation is used herein to portray polypeptide sequences: the left-hand end of a polypeptide sequence is the amino-terminus; the right-hand end of a polypeptide sequence is the carboxyl-terminus.

It will be appreciated, of course, that the peptides or polypeptides of the invention may incorporate amino acid residues which are modified without affecting activity. For example, the termini may be derivatized to include blocking groups, i.e. chemical substituents suitable to protect and/or stabilize the N- and C-termini from "undesirable degradation", a term meant to encompass any type of enzymatic, chemical or biochemical breakdown of the peptide or polypeptide antibody or fragment thereof at its termini which is likely to affect the function of the peptide or polypeptide in preferentially binding with a PF4/heparin complex relative to either PF4 or heparin alone, i.e. sequential degradation of the peptide or polypeptide at a terminal end thereof.

Blocking groups include protecting groups conventionally used in the art of peptide chemistry which will not adversely affect the in vivo activity of the peptide or polypeptide antibody or fragment thereof. For example, suitable N-terminal blocking groups can be introduced by alkylation or acylation of the N-terminus. Examples of suitable N-terminal blocking groups include $C_1$-$C_5$ branched or unbranched alkyl groups, acyl groups such as formyl and acetyl groups, as well as substituted forms thereof, such as the acetamidomethyl (Acm) group. Desamino analogs of amino acids are also useful N-terminal blocking groups, and can either be coupled to the N-terminus of the peptide or used in place of the N-terminal reside. Suitable C-terminal blocking groups, in which the carboxyl group of the C-terminus is either incorporated or not, include esters, ketones or amides. Ester or ketone-forming alkyl groups, particularly lower alkyl groups such as methyl, ethyl and propyl, and amide-forming amino groups such as primary amines (—$NH_2$), and mono- and di-alkylamino groups such as methylamino, ethylamino, dimethylamino, diethylamino, methylethylamino and the like are examples of C-terminal blocking groups. Descarboxylated amino acid analogues such as agmatine are also useful C-terminal blocking groups and can be either coupled to the peptide's C-terminal residue or used in place of it. Further, it will be appreciated that the free amino and carboxyl groups at the termini can be removed altogether from the peptide to yield desamino and descarboxylated forms thereof without affect on peptide activity in preferentially binding with a PF4/heparin complex relative to either PF4 or heparin alone.

Other modifications can also be incorporated without adversely affecting the biological activity of the peptide or polypeptide antibody or fragment thereof in preferentially binding with a PF4/heparin complex relative to either PF4 or heparin alone. Such modifications include, but are not limited to, substitution of one or more of the amino acids in the natural L-isomeric form with amino acids in the D-isomeric form. Thus, the peptide may include one or more D-amino acid residues, or may comprise amino acids which are all in the D-form. Retro-inverso forms of peptides in accordance with the present invention are also contemplated, for example, inverted peptides in which all amino acids are substituted with D-amino acid forms.

Acid addition salts of the peptide or polypeptide antibody or fragment thereof are also contemplated as functional equivalents. Thus, a peptide in accordance with the present invention treated with an inorganic acid such as hydrochloric, hydrobromic, sulfuric, nitric, phosphoric, and the like, or an organic acid such as an acetic, propionic, glycolic, pyruvic, oxalic, malic, malonic, succinic, maleic, fumaric, tartaric, citric, benzoic, cinnamic, mandelic, methanesulfonic, ethanesulfonic, p-toluenesulfonic, salicyclic and the like, to provide a water soluble salt of the peptide suitable for use in preferentially binding with a PF4/heparin complex relative to either PF4 or heparin alone.

The present invention also includes analogs of polypeptides or peptides of the invention. Analogs can differ from naturally occurring proteins or peptides by conservative amino acid sequence differences or by any of the modifications described herein or known in the art which do not affect sequence, or by both. Modifications can be made as described herein or by using any technique known to the skilled artisan.

For example, conservative amino acid changes may be made, which although they alter the primary sequence of the protein or peptide, do not normally alter its function. Conservative amino acid substitutions typically include substitutions within the following groups:

glycine, alanine;
valine, isoleucine, leucine;
aspartic acid, glutamic acid;
asparagine, glutamine;
serine, threonine;
lysine, arginine;
phenylalanine, tyrosine.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included in the invention are polypeptides which have been modified using ordinary molecular biological techniques so as to improve their resistance to proteolytic degradation or to optimize solubility properties or to render them more suitable for preferentially binding with a PF4/heparin complex relative to either PF4 or heparin alone. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

In any of the compositions and methods of the invention described herein, one or more of a functional element, an analog, an epitope, and a chimeric peptide can be used in place of a polypeptide or peptide antibody or fragment thereof. This enables the use of a smaller peptide in the inventive compositions having similar or greater activity than the corresponding larger peptide or polypeptide of the invention. Methods for identifying a functional element, an epitope, an analog or a chimeric polypeptide for any of the peptides or polypeptides of the invention are described herein. By way of example and not by limitation, such functional elements, analogs, epitopes and chimeric peptides can be prepared using recombinant technology or isolated from natural sources. Alternatively, they can be prepared synthetically by using any peptide synthesis method known in the art, such as a solid-phase peptide synthesis method.

In one embodiment, the polypeptide of the invention is present in the inventive composition as an isolated polypeptide. The isolated polypeptide can be prepared by any method known to the skilled artisan for preparing an isolated polypeptide.

For example, the isolated polypeptide of the invention can be obtained by preparing and purifying a recombinant version of any of the polypeptides of the invention described herein. Molecular biology techniques for the preparation of recombinant polypeptides are well known in the art, and are described for example in Sambrook et al., 1989, *Molecular Cloning: A Laboratory Manual*, Cold Spring Harbor Laboratory, New York; Ausubel et al., 1994, *Current Protocols in Molecular Biology*, John Wiley & Sons, New York), and Gerhardt et al., eds., 1994, *Methods for General and Molecular Bacteriology*, American Society for Microbiology, Washington, D.C. Protein purification methods are also well known in the art, and are described, for example in Deutscher et al. (ed., 1990, *Guide to Protein Purification*, Harcourt Brace Jovanovich, San Diego).

As used herein, an "analog" of a peptide or polypeptide antibody or fragment thereof means a peptide or polypeptide which has been modified from the naturally occurring peptide or polypeptide by any of the modifications described herein or known to the skilled artisan, but which still exhibits activity similar to the naturally occurring peptide or polypeptide in preferentially binding with a PF4/heparin complex relative to either PF4 or heparin alone.

As used herein, a "chimeric peptide" or "chimeric polypeptide" means a peptide or polypeptide antibody or fragment thereof which comprises at least a portion of a naturally occurring peptide or polypeptide and at least a portion of a peptide or polypeptide with which it is normally not found together with in nature, but which still exhibits activity similar to the naturally occurring peptide or polypeptide of the invention in preferentially binding with a PF4/heparin complex relative to either PF4 or heparin alone.

As used herein, a "functional element" of a peptide or a polypeptide antibody or fragment thereof means a portion of a peptide or polypeptide of the invention which participates in the pathogenesis of HIT/HITT. By way of example and not by limitation, the functional element can be a peptide, a peptide analog or an epitope of a polypeptide of the invention, a chimeric peptide thereof or an analog of a chimeric peptide thereof. A method of identifying a functional element of a peptide or polypeptide of the invention is described herein.

As used herein, an "epitope" of a peptide or a polypeptide of the invention means a portion of a peptide or polypeptide of the invention which is exposed at the surface of the peptide or polypeptide of the invention or which is accessible to an antigen (i.e. PF4/heparin complex or PF4/glycosaminoglycan complex) of a peptide or polypeptide of the invention.

As used herein, the term "vector" means a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated viral vectors, retroviral vectors, and the like.

As used herein, the term "expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses that incorporate the recombinant polynucleotide.

As used herein, the term "promoter/regulatory sequence" means a nucleic acid sequence which is required for expression of a gene product operably linked to the promoter/regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

An "inducible" promoter is a nucleotide sequence which, when operably linked with a polynucleotide which encodes or specifies a gene product, causes the gene product to be produced in a living human cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a living human cell substantially only if the cell is a cell of the tissue type corresponding to the promoter.

Description

The invention relates to compositions, kits and methods comprising a monoclonal antibody which shares key functional properties with the polyclonal antibodies which participate in the pathogenesis of heparin induced thrombocytopenia/thrombosis (HIT/HITT) in a mammal. The monoclonal antibody is exemplified herein by a murine monoclonal antibody which preferentially binds with a PF4/heparin complex relative to the binding of the antibody with either PF4 or heparin alone. The monoclonal antibody also binds specifically with PF4 in a complex with other glycosaminoglycans besides heparin, and also activates platelets. The monoclonal antibody is thus useful in methods for diagnosing and treating HIT/HITT in a mammal. A humanized version of the monoclonal antibody is also included, along with a process for humanizing the monoclonal antibody.

The invention includes a composition comprising a monoclonal antibody which is capable of binding specifically with a PF4/heparin complex. The monoclonal antibody of the invention preferentially binds with the PF4/heparin complex relative to the binding of the antibody with either PF4 or heparin alone. The monoclonal antibody can be any type of monoclonal antibody known to the skilled artisan or yet to be known. By way of example and not by limitation, such monoclonal antibody types include humanized antibodies, synthetic antibodies and phage displayed antibodies.

Monoclonal antibodies directed against full length or peptide fragments of a protein or peptide may be prepared using any well known monoclonal antibody preparation procedures, such as those described, for example, in Harlow et al. (1988, In: Antibodies, A Laboratory Manual, Cold Spring Harbor, N.Y.) and in Tuszynski et al. (1988, Blood, 72:109-115). Quantities of the desired peptide may also be synthesized using chemical synthesis technology. Alternatively, DNA encoding the desired peptide may be cloned and expressed from an appropriate promoter sequence in cells suitable for the generation of large quantities of peptide. Monoclonal antibodies directed against the peptide are generated from mice immunized with the peptide using standard procedures as referenced herein.

Nucleic acid encoding the monoclonal antibody obtained using the procedures described herein may be cloned and sequenced using technology which is available in the art, and is described, for example, in Wright et al. (1992, Critical Rev, in Immunol. 12(3,4):125-168) and the references cited therein. Further, the antibody of the invention may be "humanized" using the technology described in Wright et al., (supra) and in the references cited therein, and in Gu et al. (1997, Thrombosis and Hematocyst 77(4):755-759).

In one embodiment, the monoclonal antibody of the invention is a humanized monoclonal antibody. Humanized monoclonal antibodies are useful for reducing the immunogenicity of a monoclonal antibody in a human.

Several approaches are known in the art to reduce the immunogenicity of murine monoclonal antibodies in humans. One approach is to construct chimeric molecules which have murine variable regions (Fab), which retain antigenic specificity, connected to human constant regions (Fc). This can be accomplished using established techniques in genetic engineering including the following: 1) transfection of human and murine chain gene constructs into a non-secreting myeloma cell line (Morrison et al., 1984, Proc. Natl. Acad. Sci. USA, 81: 6851-6855); or 2) gene targeting through homologous recombination (Fell et al., 1989, Proc. Natl. Acad. Sci. USA. 86: 8507-8511). However, immune responses to the variable region of the chimeric antibodies still occur, and thus limit their therapeutic use in some cases (Knight et al., 1995, Mol. Immunol. 32, 1271-1281).

In order to further reduce the human immune response to murine monoclonal or chimeric antibodies, techniques for humanizing antibodies have been developed (Jones et al., 1986, Nature 321: 522-525; Reichman et al., 1988, Nature 332: 323-327). These techniques involve genetic grafting of the complementary-determining regions (CDR) of the murine antibody onto the human heavy and light chain framework residues. The original technique described by Reichman et. al. involves producing a human variable region with the desired specificity of the murine hypervariable region. Murine hypervariable (HV) primers with sequences complementary to the murine HV region are synthesized with flanking human framework sequences corresponding to the human HV region. These murine HV primers, in addition to nucleotides and DNA polymerase, are added to a plasmid containing the human variable region gene. This reaction results in a humanized murine variable gene (huV), containing human framework regions and murine HV regions. The humanized variable region is next inserted into a plasmid containing a human constant region gene.

This procedure was employed to create humanized heavy and light chains which were then cotransfected into a non-secreting myeloma cell line. Subsequent refinements of this basic procedure have resulted in a process for producing humanized antibodies with affinities and biological properties comparable to that of the parent murine monoclonal antibody (Emery et al., 1995, Strategies for humanizing antibodies, In: Antibody Engineering, $2^{nd}$ ed., Ed. Borrebaeck CAK) pp 159-183, Oxford University Press, Oxford). This technology can be similarly utilized to create functional humanized Fab' fragments in bacterial cells (Carter et. al., 1992. Bio/Technology, 10: 163-168).

For the purposes of the present invention, the latter technique of humanizing antibodies using CDR grafting to generate humanized monoclonal antibodies or Fab derivatives thereof is the preferred technique for reducing the immunogenicity of murine monoclonal antibodies in humans.

Antibodies displayed at the surface of a bacteriophage are also contemplated by the antibodies of the invention. Bacteriophage which encode the desired antibody may be engineered such that the protein is displayed on the surface thereof in such a manner that it is available for binding to its corresponding binding protein, e.g., the antigen against which the antibody is directed. Thus, when bacteriophage which express a specific antibody are incubated in the presence of a cell which expresses the corresponding antigen, the bacteriophage will bind to the cell. Bacteriophage which do not express the antibody will not bind to the cell. Such panning techniques are well known in the art and are described for example, in Wright et al., (supra).

To generate a phage antibody library, a cDNA library is first obtained from mRNA which is isolated from cells, e.g., the hybridoma, which express the desired protein to be expressed on the phage surface, e.g., the desired antibody. cDNA copies of the mRNA are produced using reverse transcriptase. cDNA which specifies immunoglobulin fragments are obtained by PCR and the resulting DNA is cloned into a suitable bacteriophage vector to generate a bacteriophage DNA library comprising DNA specifying immunoglobulin genes. The procedures for making a bacteriophage library comprising heterologous DNA are well known in the art and are described, for example, in Sambrook et al. (1989, Molecular Cloning: A Laboratory Manual, Cold Spring Harbor, N.Y.).

Processes such as those described above, have been developed for the production of human antibodies using M13 bacteriophage display (Burton et al., 1994, Adv. Immunol. 57:191-280). Essentially, a cDNA library is generated from mRNA obtained from a population of antibody-producing cells. The mRNA encodes rearranged immunoglobulin genes and thus, the cDNA encodes the same. Amplified cDNA is cloned into M13 expression vectors creating a library of phage which express human Fab fragments on their surface. Phage which display the antibody of interest are selected by antigen binding and are propagated in bacteria to produce soluble human Fab immunoglobulin. Thus, in contrast to conventional monoclonal antibody synthesis, this procedure immortalizes DNA encoding human immunoglobulin rather than cells which express human immunoglobulin.

The procedures just presented describe the generation of phage which encode the Fab portion of an antibody molecule. However, the invention should not be construed to be limited solely to the generation of phage encoding Fab antibodies. Rather, phage which encode single chain antibodies (scFv/ phage antibody libraries) are also included in the invention. Fab molecules comprise the entire Ig light chain, that is, they comprise both the variable and constant region of the light chain, but include only the variable region and first constant region domain (CH1) of the heavy chain. Single chain antibody molecules comprise a single chain of protein comprising the Ig Fv fragment. An Ig Fv fragment includes only the variable regions of the heavy and light chains of the antibody, having no constant region contained therein. Phage libraries comprising scFv DNA may be generated following the procedures described in Marks et al., 1991, J. Mol. Biol. 222: 581-597. Panning of phage so generated for the isolation of a desired antibody is conducted in a manner similar to that described for phage libraries comprising Fab DNA.

The invention should also be construed to include synthetic phage display libraries in which the heavy and light chain variable regions may be synthesized such that they include nearly all possible specificities (Barbas, 1995, Nature Medicine 1:837-839; de Kruif et al. 1995, J. Mol. Biol. 248:97-105).

In one embodiment, the monoclonal antibody of the invention comprises a heavy chain polypeptide having an amino acid sequence which shares at least about 80% homology with SEQ ID NO:1 (FIG. 7A). Preferably, the heavy chain polypeptide is about 85% homologous, more preferably about 90% homologous, even more preferably about 95% homologous, and most preferably about 99% homologous to the heavy chain polypeptide of SEQ ID NO:1. Even more preferably, the monoclonal antibody of the invention comprises a heavy chain polypeptide which is SEQ ID NO:1. Also, in this embodiment the monoclonal antibody of the invention comprises a light chain polypeptide having an amino acid sequence which shares at least about 80% homology with SEQ ID NO:2 (FIG. 7B). Preferably, the light chain polypeptide is about 85% homologous, more preferably about 90% homologous, even more preferably about 95% homologous, and most preferably about 99% homologous to the light chain polypeptide of SEQ ID NO:2. Even more preferably, the monoclonal antibody of the invention comprises a light chain polypeptide which is SEQ ID NO:2.

The determination of percent homology (i.e. percent identity) described herein between two amino acid or nucleotide sequences can be accomplished using a mathematical algorithm. For example, a mathematical algorithm useful for comparing two sequences is the algorithm of Karlin and Altschul (1990, Prc. Natl. Acad. Sci. USA 87:2264-2268), modified as in Karlin and Altschul (1993, Proc. Natl. Acad. Sci. USA 90:5873-5877). This algorithm is incorporated into the NBLAST and XBLAST programs of Altschul, et al. (1990, J. Mol. Biol. 215:403-410), and can be accessed, for example, at the National Center for Biotechnology Information (NCBI) world wide web site having the universal resource locator "www.ncbi.nlm.nih.gov/BLAST". Blast nucleotide searches can be performed with NBLAST program (designated "blastn" at NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with XLBLAST Program (designated "blastn" at the NCBI web site) or the NCBI "blastp" program, using the following parameters: expectation value 10.0, BLOSUM62 scoring matrix to obtain amino acid sequences homologous to a protein molecule described herein To obtain gapped alignments for comparison purposes, Gapped BLAST can be utilized as described in Altschul et al. (1997, Nucleic Acids Res. 25:3389-3402). Alternatively, PSI-Blast or PHI-Blast can be used to perform an integrated search which detects distant relationships between molecules (id.) and relationships between molecules which share a common pattern. When utilizing BLAST, Gapped Blast, PSI-Blast, and PHI-Blast programs, the default parameters of the respective programs (e.g., XBLAST and NBLAST) can be used. See the world wide web having the universal locator www.ncbi.nlm.nih.gov.

The percent identity between two amino acid or nucleotide sequences can be determined using techniques similar to those described above, with or without allowing gaps. In calculating percent identity, typically exact matches are counted.

In a preferred aspect, the monoclonal antibody of the invention is a murine monoclonal antibody comprising the heavy chain polypeptide of SEQ ID NO: 1 and the light chain polypeptide of SEQ ID NO:2, and is referred to herein as "KKO".

Deposit

Hybridoma KKO, was deposited on Jul. 30, 2004, with the American Type Culture Collection (ATCC) of 10801 University Blvd., Manassas, Va., 20110-2209 USA, and accorded ATCC accession number PTA-6133.

In one embodiment, the monoclonal antibody of the invention is capable of activating platelets in the presence of a PF4/heparin complex.

In another embodiment, the monoclonal antibody of the invention is also capable of binding specifically with a complex of PF4 and a glycosaminoglycan (GAG) which is not heparin. Preferably, the monoclonal antibody of the invention preferentially binds with the complex of PF4/GAG relative to the binding of the antibody with either PF4 or the GAG alone. Non-limiting examples of such other glycosaminoglycans include chondroitin sulfates A, B and C, heparan sulfate, dextran sulfate and low molecular weight heparin. Other glucanated sulfates known in the art as recognized by human polyclonal HIT/HITT antibodies are included within the GAGs of the invention, and are discussed, for example, in Greinacher et al., 1995, Thrombosis and Haemostasis, 74:886-892.

The invention also includes a composition comprising an isolated nucleic acid, wherein the isolated nucleic acid encodes one or more of a heavy chain and a light chain polypeptide of a monoclonal antibody which is capable of binding specifically with a PF4/heparin complex. The antibody comprised of the heavy and light chain polypeptides encoded by the one or more isolated nucleic acids of the invention preferentially binds with the PF4/heparin complex relative to the binding of the antibody with either PF4 or heparin alone.

The isolated nucleic acid which encodes the heavy chain polypeptide has a nucleotide sequence which shares at least about 80% homology with SEQ ID NO:3 (FIG. 7C). Preferably, the isolated nucleic acid which encodes the heavy chain polypeptide is about 85% homologous, more preferably about 90% homologous, even more preferably about 95% homologous, and most preferably about 99% homologous to the isolated nucleic acid corresponding to SEQ ID NO:3. Even more preferably, the isolated nucleic acid which encodes the heavy chain polypeptide is the isolated nucleic acid of SEQ ID NO:3.

The isolated nucleic acid which encodes the light chain polypeptide has a nucleotide sequence which shares at least about 80% homology with SEQ ID NO:4 (FIG. 7D). Preferably, the isolated nucleic acid which encodes the light chain polypeptide is about 85% homologous, more preferably about 90% homologous, even more preferably about 95% homologous, and most preferably about 99% homologous to the isolated nucleic acid corresponding to SEQ ID NO:4. Even more preferably, the isolated nucleic acid which encodes the light chain polypeptide is the isolated nucleic acid of SEQ ID NO:4.

In embodiments of the invention where the inventive composition comprises an isolated nucleic acid, the isolated nucleic acid is preferably present in an amount effective to transform a mammalian cell to provide expression of the monoclonal antibody at a level of expression effective to result in production of the monoclonal antibody in the mammal at a level sufficient to provide competitive inhibition of the specific binding of a polyclonal antibody within the mammal with a PF4/heparin complex.

The isolated nucleic acid can be either alone as a "naked" nucleic acid, such as a linearized nucleic acid, or as a component of any type of vector suitable for transfecting a mammalian cell described herein or known in the art. Preferably, the isolated nucleic acid is a recombinant polynucleotide component of a viral or plasmid expression vector suitable for transfecting a mammalian cell, and is operably linked to the appropriate regulatory elements to provide a high level of expression of the transgene once a targeted mammalian cell is transformed with the isolated nucleic acid. Examples of preferred vectors include adenovirus, retrovirus, lentivirus and adeno-associated virus vectors. Techniques for using such vectors to transfect a mammalian cell are known in the art. Appropriate promoter/regulatory elements to be included in the vector used will be apparent to the skilled artisan.

When any one of the polypeptides of the invention are to be administered to a mammal or to a tissue of a mammal in a method of the invention for the purpose of exerting a beneficial effect in the mammal, the invention should be construed to include delivery of the polypeptide via delivery of an isolated nucleotide sequence encoding the peptide. Expression of the peptide from the nucleotide sequence so delivered to the desired tissue is effective administration of the peptide to the cell or tissue.

In another embodiment, the inventive composition is in the form of a pharmaceutical composition comprising a pharmaceutically acceptable carrier. Such a pharmaceutical composition may consist of the inventive composition alone as the active ingredient, in a form suitable for administration to a subject, or the pharmaceutical composition may comprise the inventive composition as the active ingredient and one or more pharmaceutically acceptable carriers, one or more additional ingredients, or some combination of these. The active ingredient may be present in the pharmaceutical composition in the form of a pharmaceutically acceptable salt, such as in combination with a physiologically acceptable cation or anion, as is well known in the art.

As used herein, the term "pharmaceutically acceptable carrier" means a chemical composition with which the active ingredient may be combined and which, following the combination, can be used to administer the active ingredient to a subject.

As used herein, the term "pharmaceutically acceptable salt" means a salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to any mammal. Modification of pharmaceutical compositions suitable for administration to humans in order to render the compositions suitable for administration to various mammals is well understood, and the ordinarily skilled veterinary pharmacologist can design and perform such modification with merely ordinary, if any, experimentation.

Pharmaceutical compositions that are useful in the methods of the invention may be prepared, packaged, or sold in formulations suitable for any route of administration known to the skilled artisan, including, by way of example and not by limitation, oral, parenteral, topical, ocular, inhalation, intrauterine, intravesicular, intraurethral and buccal routes of administration. The pharmaceutical composition can be administered to a mammal by any route of administration known to the skilled artisan, such as those described above, and by any method of administering a pharmaceutical composition to a mammal known in the art. A pharmaceutical composition of the invention may be prepared, packaged, or sold in bulk, as a single unit dose, or as a plurality of single unit doses.

As used herein, a "unit dose" is a discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

Controlled or sustained-release formulations of a pharmaceutical composition of the invention may be made using conventional technology.

A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

As used herein, an "oily" liquid is one which comprises a carbon-containing liquid molecule and which exhibits a less polar character than water.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically-controlled release tablets. Tablets may further comprise a sweetening agent, a flavoring agent, a coloring agent, a preservative, or some combination of these in order to provide pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Liquid formulations of a pharmaceutical composition of the invention which are suitable for oral administration may be prepared, packaged, and sold either in liquid form or in the form of a dry product intended for reconstitution with water or another suitable vehicle prior to use.

Liquid suspensions may be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g. polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Formulations suitable for topical administration include, but are not limited to, liquid or semi-liquid preparations such as liniments, lotions, oil-in-water or water-in-oil emulsions such as creams, ointments or pastes, and solutions or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics;

antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, *Remington's Pharmaceutical Sciences*, Mack Publishing Co., Easton, Pa., which is incorporated herein by reference.

Typically dosages of the composition of the invention which may be administered to an animal, preferably a human, range in amount from 1 microgram to about 100 grams per kilogram of body weight of the animal. While the precise dosage administered will vary depending upon any number of factors, including but not limited to, the type of animal and type of disease state being treated, the age of the animal and the route of administration. Preferably, the dosage of the composition will vary from about 1 mg to about 10 g per kilogram of body weight of the animal. More preferably, the dosage will vary from about 10 mg to about 1 g per kilogram of body weight of the animal.

The composition may be administered to an animal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the animal, etc.

Any of the pharmaceutical compositions of the invention may further comprise one or more compounds known in the art to enhance and facilitate drug administration.

Other possible formulations, such as nano particles, liposomes, resealed erythrocytes, and immunologically based systems such as antibody targeting systems may also be used to administer the inventive composition according to the methods of the invention described herein.

In one embodiment, the composition of the invention comprising the monoclonal antibody is in the form of a pharmaceutical composition.

The invention also includes a method of making a humanized monoclonal antibody which is capable of binding specifically with a PF4/heparin complex. The monoclonal antibody preferentially binds with the PF4/heparin complex relative to the binding of the antibody with either PF4 or heparin alone.

The method comprises obtaining a monoclonal antibody which is capable of binding specifically with a PF4/heparin complex. The monoclonal antibody preferentially binds with the PF4/heparin complex relative to the binding of the antibody with either PF4 or heparin alone. The monoclonal antibody can be obtained from any source, either natural or synthetic. When the monclonal antibody is prepared synthetically, any method known to the skilled artisan for the preparation of a monoclonal antibody may be used. An example of such a method is described herein in the Experimental Examples.

The humanized monoclonal antibody preferentially binds the PF4/heparin complex relative to the binding of the antibody with either PF4 or heparin alone.

In one aspect, the monoclonal antibody used in the method comprises a heavy chain polypeptide having an amino acid sequence which shares at least about 80% homology with the polypeptide of SEQ ID NO:1, and comprises a light chain polypeptide having an amino acid sequence which shares at least about 80% homology with the polypeptide of SEQ ID NO:2. Preferably, the monoclonal antibody used in the method comprises a heavy chain polypeptide having the amino acid sequence of SEQ ID NO:1, and comprises a light chain polypeptide having the amino acid sequence of SEQ ID NO:2.

The invention also includes a method of diagnosing heparin-induced thrombocytopenia/thrombosis (HIT/HITT) in a mammal. The method comprises assessing the level of a polyclonal antibody which binds specifically with a PF4/heparin complex in a sample obtained from the mammal and comparing the level assessed with a positive control sample for HIT/HITT. The positive control sample comprises any of the monoclonal antibodies or fragments thereof described in the inventive compositions. When the level or concentration of the polyclonal antibody in the sample obtained from the mammal is statistically similar to the level of the monoclonal antibody present in the positive control sample, then HIT/HITT is diagnosed in the mammal. The mammal can be any mammal but is preferably a human.

The method comprises obtaining a sample of a bodily fluid or tissue from the mammal. By way of example, and not by limitation, the bodily fluid or tissue can be a blood sample, a serum sample, a biopsy sample, a cerebrospinal fluid sample, a urine sample, an ascites sample, a pleural effusion sample, a clot tissue sample, or any other tissue sample.

The method also includes assessing the level of a polyclonal antibody in the sample which binds specifically with a PF4/heparin complex. The polyclonal antibody preferentially binds with the PF4/heparin complex relative to the binding of the polyclonal antibody with either PF4 or heparin alone. The level of the polyclonal antibody can be assessed by any method known to the skilled artisan for assessing the level or concentration of an antibody in a sample.

Preferred methods for assessing the level of the polyclonal antibody in the sample include an ELISA assay, a Western Blotting assay, a serotonin release assay, a platelet aggregation assay, a lumi-aggregometry assay, and a flow cytometry assay. Such methods are known in the art or described herein. Briefly, an ELISA assay can be used in which the antigen (PF4/heparin complex) is coated on microtiter plates and the presence of antigen-specific antibodies is detected using enzyme-labelled anti-human or anti-mouse antibodies (See, Arepally et al., 1995. Am. J. Clin. Pathol., 104:648). A Western blotting assay can be used in which the PF4/heparin complex is the antigen (See, Harlow et al., 1988, Antibodies: A Laboratory Manual, N.Y., Cold Spring Harbor Laboratory, 479-504). A serotonin release assay can be used in which platelets are loaded with radiolabeled serotonin and incubated in the presence of heparin or buffer and HIT/HITT antibodies. A positive result is indicated by platelet activation and the release of radiolabeled serotonin into the supernatant in the presence of heparin, but not in the presence of buffer (See, Sheridan et al., 1986, Blood, 67:27-30).

Variations upon the platelet activation assay include the platelet aggregation assay, which employs a platelet aggregometer to optically detect the activation of platelets, the heparin induced platelet activation assay, which employs a visual endpoint of transparency for detecting platelet activation, and lumi-aggregometry, which measures luminescence detected via ATP release as an endpoint for platelet activation (Stewart et al., 1995, British J. Haematol. 91:173-177).

Additionally, flow cytometry assays can be used to assess the level of the polyclonal antibody in the sample. Briefly, fluorescent labeled antibodies to platelets are used to measure platelet activation by HIT/HITT antibodies in the presence of heparin or buffer using a flow cytometer instrument. The generation of activated platelets is detected by the binding of activation-specific markers (Tomer, A., 1997, Br. J. Haematol., 98:648-656) or by microparticle generation (Lee et al., 1996, Br. J. Haematol., 95:724-731).

Other methods known in the art for assessing the level or concentration of a polyclonal antibody in a sample can be used, such as, by way of example and not by limitation, chromatographic methods or other immunological methods (See, for example, Harlow et al., 1988, Antibodies: A Laboratory Manual, Cold Spring Harbor, New York). For example, particle-gel immunoassay methods can be used which employ a particle gel immunoassay commonly employed in transfusion medicine. Red high density polystyrene beads coated with human PF4/heparin complexes are exposed to HIT/HITT antibodies in a reaction chamber containing a buffered sephacryl gel matrix. The beads are centrifuged and agglutination at the top of the dispersed gel is interpreted as positive detection. Enzyme immunoassay (EIA) methods can also be used. An EIA is a fluid phase assay which measures the binding of HIT/HITT antibodies to biotinylated-PF4/heparin complexes in solution (See, e.g. Newman et al., 1998, Thrombosis and Haemostasis. 80:292-297).

The method also includes comparing the level of the polyclonal antibody in the sample assessed as described above with the level of a monoclonal antibody which is specific for the PF4/heparin complex in a positive control sample for HIT/HITT. The level of the monoclonal antibody present in the positive control sample can be assessed by any method known to the skilled artisan for measuring the level or concentration of an antibody in a sample. Preferred methods for assessing the level of the monoclonal antibody in the sample include an ELISA assay, a serotonin release assay, a platelet aggregation assay, a lumi-aggregometry assay, and a flow cytometry assay.

Other methods known in the art for assessing the level or concentration of a monoclonal antibody such as, by way of example and not by limitation, chromatographic methods or other immunological methods can also be used to detect the level of the monoclonal antibody in the positive control sample.

The method also includes determining from the level of the polyclonal antibody and the level of the monoclonal antibody assessed as described above, whether the level of the polyclonal antibody in the sample obtained from the mammal is statistically similar to the level of the monoclonal antibody in the positive control sample for HIT/HITT. The determination of whether the levels of the monoclonal and polyclonal antibodies are statistically similar can be made by any statistical method known to the skilled artisan. The ordinarily skilled artisan will be aware that the percent variation from the positive control which could be used as a cut-off point for the diagnosis of HIT/HITT depends upon the type of method used to assess the levels of antibodies in the sample, and is calibrated using the positive control antibodies and negative controls (i.e. from normal donors or blank controls). Each assay method has separate criteria for determining a positive result, and tropically employs three standard deviations from negative controls for the positive control to be considered positive. Each of the methods discussed above for assessing antibody levels in a sample discuss in the cited references the criteria for a positive reaction for the particular type of test.

The range of concentrations appropriate for use as the concentration of the monoclonal antibody in a positive control sample for HIT/HITT will vary from about 1 microgram per milliliter to about 1 milligram per milliliter. Preferably, the concentration of the monoclonal antibody ranges from about 50 to about 200 micrograms per milliliter, and more preferably, from about 80 to about 150 micrograms per milliliter.

When the level or concentration of the polyclonal antibody present in the original sample of a body fluid or tissue obtained from the mammal is statistically similar to the level of the monoclonal antibody present in the positive control sample, then HIT/HITT is diagnosed in the mammal.

In another embodiment, the method does not include diagnosing HIT/HITT in a mammal, but instead involves simply assessing the level of the polyclonal antibody in the sample obtained from the mammal. In this embodiment, the method comprises obtaining a sample of a bodily fluid or tissue from the mammal. The bodily fluid or tissue can be any of those described herein.

The method also includes assessing the level in the sample of a polyclonal antibody which binds specifically with a PF4/heparin complex and which preferentially binds with the PF4/heparin complex relative to the binding of the polyclonal antibody with either PF4 or heparin alone. The level of the polyclonal antibody in the sample can be assessed by any method known to the skilled artisan or described herein for assessing the level or concentration of an antibody in a sample.

The method also includes comparing the level of the polyclonal antibody in the sample assessed as described above with the level of a monoclonal antibody in a reference standard containing the monoclonal antibody. The monoclonal antibody is specific for the PF4/heparin complex and preferentially binds with the PF4/heparin complex relative to the binding of the monoclonal antibody with either PF4 or heparin alone. The level of the monoclonal antibody in the reference standard can be assessed by any method known to the skilled artisan or described herein for measuring the level or concentration of an antibody in a sample. Preferred methods for assessing the level of the monoclonal antibody in the reference standard include an ELISA assay, a serotonin release assay, a platelet aggregation assay, a lumi-aggregometry assay, and a flow cytometry assay.

The monoclonal antibody can be any of the monoclonal antibodies described herein in the inventive compositions, or a functional element or fragment thereof. A preferred monoclonal antibody is the murine monoclonal antibody KKO, or a functional element, fragment or humanized version thereof.

The method also includes determining, from the comparison described above, the level of the polyclonal antibody in the sample obtained from the mammal, thereby determining the level of a polyclonal antibody in the mammal which binds specifically with a PF4/heparin complex and which preferentially binds with the PF4/heparin complex relative to the binding of the polyclonal antibody with either PF4 or heparin alone.

The invention also includes a method of identifying a functional element of an antibody, wherein the functional element participates in the pathogenesis of HIT/HITT in a mammal. The method comprises preparing one or more deletion mutants of a monoclonal antibody which binds specifically with a PF4/heparin complex, and which preferentially binds with the PF4/heparin complex relative to the binding of either PF4 or heparin alone. The deletion mutant can be a polypeptide having either a deletion or a substitution mutation. Methods of preparing deletion or substitution mutants of polypeptides and antibodies are known in the art (See, for example, Sambrook et al., 1989, *Molecular Cloning: A Laboratory Manual*, Cold Spring Harbor Laboratory, New York and Ausubel et al., 1994, *Current Protocols in Molecular Biology*, John Wiley & Sons, New York). The one or more deletion mutants prepared lack a portion of the amino acid sequence of the Fab region of the monoclonal antibody.

The method also includes assessing the ability of each of the deletion mutants so prepared to bind specifically with a PF4/heparin complex, and to preferentially bind with the PF4/heparin complex relative to the binding of the deletion mutant with either PF4 or heparin alone. The assessment of such binding can be performed using any immunological or other assay know to the skilled artisan or described herein for assessing the binding of an antibody to an antigen. Examples of such methods are described herein or known in the art. For example, the determination of loss or gain of the ability of a deletion mutant to bind specifically with a PF4/heparin complex can be performed by measuring the association and disassociation constants for antigen-antibody interactions (See, e.g., Tomlinson, G. 1988, Trends in Pharm. Sci., 9:159-162).

The method also includes identifying from the binding ability assessed as described above for each of the deletion mutants, one or more of the deletion mutants which does not preferentially bind with the PF4/heparin complex relative to the binding of the deletion mutant with either PF4 or heparin alone. Based upon the one or more deletion mutants so identified, the corresponding deleted portion of the amino acid sequence of the monoclonal antibody which participates in the preferential binding of the antibody with the PF4/heparin complex is determined. By determining which portion of the amino acid sequence of the monoclonal antibody participates in preferential binding with a PF4/heparin complex, a functional element of an antibody which participates in the pathogenesis of HIT/HITT in a mammal is identified.

In addition to the method discussed above, other methods known in the art for identifying a functional element of an antibody can be used. For example, anti-peptide antibodies, deletion/substitution mutants, chimeric antibodies and other peptide inhibition methods can be used to identify a functional element of the monoclonal antibody of the invention which participates in the pathogenesis of HIT/HITT in a mammal. A functional element of the antibody can be identified through the construction of chimeric or humanized antibodies which are derived from two species, such as human and mouse. Methods for constructing and evaluating chimeric antibodies are discussed above.

The invention also includes a method of treating HIT/HITT in a mammal, preferably, a human. The method comprises administering to the mammal a composition comprising the monoclonal antibody of the invention, or a functional element thereof, which binds specifically with a PF4/heparin complex, and which preferentially binds with the PF4/heparin complex relative to the binding of the monoclonal antibody with either PF4 or heparin alone. The composition is administered in an amount effective to competitively inhibit the specific binding of a polyclonal antibody in the mammal to a PF4/heparin complex, thus inhibiting the specific binding of the polyclonal antibody in the mammal with the PF4/heparin complex, thereby treating HIT/HITT in the mammal.

In the method of the invention, any of the inventive compositions disclosed herein can be administered to the mammal to be treated by any route of administration known in the art or described herein. Preferably, the inventive composition is administered parenterally (i.e. intravenously or intramuscularly).

In one aspect, the inventive composition is administered to the mammal in the form of a pharmaceutical composition. The pharmaceutical composition can be any of the pharmaceutical compositions described herein.

In the method of the invention, the use of a derivatized fragment of a monoclonal antibody (i.e. such as a derivatized Fab or $F(ab)_2$ fragment instead of the entire antibody molecule) in the inventive composition is preferred, since such fragments will retain antigen specificity without causing effector cell activation, such as platelet activation through the Fc portion of the antibody. Fab and $F(ab)_2$ fragments can be prepared and derivatized using immunological methods well known in the art (See, for example, Harlow et al., 1988, Antibodies: A Laboratory Manual. NY, Cold Spring Harbor, 479-504). Other therapeutically beneficial modifications include altering the IgG subclass isotype of a murine or humanized antibody of the invention using recombinant technology in order to abolish effector cell activation.

In the method of the invention, competitively inhibiting the specific binding of the polyclonal antibody means to substantially reduce, impede or inhibit the specific binding of the polyclonal antibody in the mammal to a PF4/heparin complex by the specific binding of a monoclonal antibody of the invention or a fragment or functional element thereof to the PF4/heparin complex. The ordinarily skilled artisan will be aware of the minimum percent inhibition that must be exhibited by the administered monoclonal antibody of the invention to be considered substantial competitive inhibition of the polyclonal antibody which is efficacious in the treatment of HIT/HITT in a mammal.

The inventive composition can be provided to the mammal either alone in "naked" form, for example as an isolated polypeptide or an isolated nucleic acid encoding the same, or it can be formulated in a vehicle suitable for delivery, such as, by way of example and not by limitation, in a complex with a cationic molecule or a liposome forming lipid, in a vector, or as a component of a pharmaceutical composition. Such vehicles are well known to the skilled artisan. The composition is preferably a humanized antibody, or a nucleic acid encoding the sane.

In one embodiment, the monoclonal antibody in the composition administered to the mammal is a monoclonal antibody comprising a heavy chain polypeptide having an amino acid sequence which shares at least about 80% homology with SEQ ID NO:1 and a light chain polypeptide having an amino acid sequence which shares at least about 80% homology with SEQ ID NO:2. Preferably, the monoclonal antibody is a humanized monoclonal antibody.

The invention also includes a method of identifying a compound which is a modulator of the specific binding of an antibody to a PF4/heparin complex. Such a compound is useful for treating HIT/HITT in a mammal, by way of example and not by limitation, by decreasing the level of specific binding of a polyclonal antibody in the human to a PF4/heparin complex, wherein the specific binding of the polyclonal antibody to the PF4/heparin complex is a factor in the pathogenesis of HIT/HITT, or by increasing the level of specific binding of a monoclonal antibody of the invention or a functional element or fragment thereof to the PF4/heparin complex in a mammal, thereby competitively inhibiting the binding of a polyclonal antibody in the mammal to the PF4/heparin complex, which is a factor in the pathogenesis of HIT/HITT. The compound can be any type of compound, and includes by way of example and not by limitation, a peptide, a polypeptide, an oligonucleotide, a nucleic acid, a drug, a ligand and a receptor. Modulating the specific binding of the antibody to the PF4/heparin complex can mean either to increase or to decrease the level of specific binding or binding affinity of the antibody to the PF4/heparin complex. The compound can operate by either directly or indirectly increasing or decreasing the level of specific binding or binding affinity of the antibody to the PF4/heparin complex by any mode of action. By way of example and not by limitation, the compound can act directly by competing for binding sites upon one or more of the antibody, PF4 or heparin, or can act indirectly by acting through a signal transduction pathway or another molecule which serves as the primary effector or through any other biological process.

The method comprises contacting the compound with the antibody and the PF4/heparin complex. The compound, the antibody and the PF4/heparin complex can be contacted in any chronological order, and need not be present together simultaneously. The components can be contacted in a liquid medium such as a solution, or on a solid surface, such as an microwell plate or a bead. A sufficient period of time is permitted for specific binding between the antibody and the PF4/heparin complex.

The method also comprises assessing the effect of the compound upon the level of specific binding of the antibody to the PF4/heparin complex. The level of specific binding can be assessed by any method known in the art or described herein for assessing the specific binding or binding affinity of an antibody to an antigen. In order to determine the effect of the compound, a comparison is made between the specific binding or binding affinity of the antibody to the PF4/heparin complex in the presence and the absence of the compound.

The effect of the compound assessed as described above is an indication of whether the compound is a modulator of the specific binding of the antibody to the PF4/heparin complex. If the compound either substantially increases or substantially decreases the level of specific binding of the antibody to the PF4/heparin complex, then a compound is identified which is a modulator of the specific binding of the antibody to the PF4/heparin complex. It will be apparent to the skilled artisan how to determine whether such increases or decreases in the level of specific binding are substantial.

In one embodiment, the antibody is a monoclonal antibody. The monoclonal antibody can be any monoclonal antibody or functional element, fragment, or humanized version thereof described herein in the inventive compositions. A preferred monoclonal antibody is the murine monoclonal antibody KKO or a functional element, fragment, or humanized version thereof.

In another embodiment, the antibody is a polyclonal antibody. The polyclonal antibody can be any polyclonal antibody which is capable of specific binding to a PF4/heparin complex and preferentially binding the PF4 heparin complex relative to either PF4 or heparin alone.

The invention also includes a kit for diagnosing HIT/HITT in a mammal. The kit comprises a positive control solution comprising a monoclonal antibody of the invention, or a functional element thereof, which binds specifically with a PF4/heparin complex. The monoclonal antibody can be any of the monclonal antibodies described herein in the inventive compositions. Preferably, the monoclonal antibody is a humanized monoclonal antibody.

The positive control solution comprises the monoclonal antibody of the invention or a functional element thereof in an amount ranging from about 1 picogram per milliliter to about 10 milligrams per milliliter, preferably from about 1 microgram per milliliter to about 200 micrograms per milliliter. The skilled artisan will be aware of appropriate variations in concentration for the monoclonal antibody in the positive control sample depending upon the sensitivity of the assay method used to assess levels of the antibody. For example, in the ELISA assay described herein, a preferred concentration range for the monoclonal antibody in the positive control ranges from about 0.1 to about 40 micrograms per milliliter, and in the serotonin release assay described herein a preferred concentration range for the monoclonal antibody in the positive control ranges from about 75 to about 150 micrograms per milliliter.

In addition to the monoclonal antibody of the invention, the positive control solution may further comprise one or more of a suitable buffer for suspending a monoclonal antibody, such as a phosphate-buffered saline buffer or a tris buffer, a stabilizer such as a glycerol solution or bovine serum albumin, and a preservative such as sodium azide.

The kit also includes an instructional material describing the using of the positive control solution for diagnosing HIT/HITT in a mammal using the inventive method described herein for diagnosing HIT/HITT in a mammal.

As used herein, an "instructional material" includes a publication, a recording, a diagram, or any other medium of expressing which can be used to communicate the usefulness of the composition of the invention in the kit for diagnosing HIT/HITT in a mammal. Optionally, or alternatively, the instructional material may describe one or more methods of diagnosing HIT/HITT in a mammal. The instructional material of the kit of the invention may, for example, be affixed to a container which contains the positive control solution of the invention or be shipped together with a container which contains the positive control solution. Alternatively, the instructional material may be shipped separately from the container with the intention that the instructional material and the positive control solution be used cooperatively by the recipient.

The invention also includes a kit for use in treating a mammal afflicted with HIT/HITT. The kit comprises a composition comprising a monoclonal antibody of the invention, or a functional element thereof, which binds specifically with a PF4/heparin complex. The composition can be any of the inventive compositions described herein. The monoclonal antibody or functional element thereof in the inventive composition preferentially binds with the PF4/heparin complex relative to the binding of the monoclonal antibody or functional element thereof with either PF4 or heparin alone. The monoclonal antibody or functional element thereof is present in the composition in an amount effective to competitively inhibit the specific binding of a polyclonal antibody in the mammal to the PF4/heparin complex.

The kit also includes an instructional material describing the use of the composition comprising the monoclonal antibody or functional element thereof for the treatment of HIT/HITT in the mammal. The instructional material is as described herein, and can be used to communicate the usefulness of the composition comprising the monoclonal antibody of the invention or functional element thereof in the kit for treating a mammal afflicted with HIT/HITT. Optionally, or alternatively, the instructional material may describe one or more methods of treating a mammal afflicted with HIT/HITT. The instructional material of the kit of the invention may, for example, be affixed to a container which contains the composition comprising the monoclonal antibody of the invention or functional element thereof, or be shipped together with the container which contains the composition comprising the monoclonal antibody of the invention or the functional element thereof. Alternatively, the instructional material may be shipped separately from the container with the intention that the instructional material and the composition be used cooperatively by the recipient.

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Example 1

The experiments discussed in this Example describe the preparation and characterization of a murine monoclonal antibody of the invention termed "KKO". The materials and methods used in the experiments of this Example are now described.

Materials

The murine myeloma cell line P3X63Ag8U.1 (P3U1) was purchased from American Type Tissue Culture Collection (Rockville, Md.). Tissue culture reagents were from Gibco BRL (Rockville, Md.). Fetal bovine serum was from Hyclone (Logan, Utah). Heparin solutions used in these studies were from Elkins-Sinn (Cherry Hill, N.J.). Reagents purchased from Amersham Pharmacia Biotech (Piscataway, N.J.) included: ECL™ chemiluminescence detection kit, Hi Trap affinity columns, ProRPC® 15 micron HR 10/10 chromatography column, 5-hydroxy [side chain-2-$^{14}$C] tryptamine creatine sulfate and the Sequenase T7 DNA polymerase kit.

Immunochemicals used in the studies described below include: anti-PF4, anti-NAP-2 and anti-IL-8 raised in rabbits from Preprotech (Rocky Hill, N.J.), swine anti-rabbit (HRP conjugate) antibody from Dako Corporation (Carpinteria, Calif.) and goat anti-human Ig G,A,M from ICN (Costa Mesa, Calif.). ImmunoPure® Monoclonal Antibody Isotyping Kit and the BCA Protein Assay Reagent Kit were obtained from Pierce Co. (Rockford, Ill.). Plates (6-well, 24-well and 96-well) for tissue culture were products of Becton Dickinson (Franklin Lakes, N.J.). Maxisorp microtiter plates used for the PF4/heparin ELISA were from Nunc Brand Products (Roskilde, Denmark). Colorimentric readings were measured using a Molecular Devices plate reader (Sunnyvale, Calif.).

Molecular biological reagents included: $pT_{7-7}$ vector, and *E. Coli* bacterial strain BL21(DE3)pLysS from Novagen (Madison, Wis.), VENT polymerase from New England Biolabs Inc. (Beverly, Mass.), the murine lambda FIX 129SV library from Stratagene (LaJolla, Calif.), TRIzol reagent and Superscript RT-PCR kit from Gibco/BRL, (Gaithersburg, Md.) and AmpliTaq from Perkin-Elmer (Branchburg, N.J.). MacVector (v. 6.0) software package was purchased from Oxford Molecular Group (Oxford, UK). All other chemicals and reagents were purchased from Sigma Chemical Co. (St. Louis, Mo.).

Patient Plasma Samples

Plasma was obtained from patients having a clinical diagnosis of HIT/HITT (Sheridan et al., 1986, Blood 67:27) and from healthy volunteers. The clinical diagnosis was confirmed using the $^{14}$C-Serotonin Release Assay (SRA) (Arepally et al., 1995, Am. J. Clin. Pathol. 104:648) and by measuring antibodies to the PF4/heparin complex using the ELISA method described below. Institutional approval was obtained for these studies.

Development of Monoclonal Antibodies to hPF4/Heparin and hPF4

Four 6-8 week old female Balb/c mice were injected intraperitoneally (IP) on Day 1 with a 50 microliter sterile solution composed of 25 microliters of PBS containing recombinant hPF4 (50 micrograms), heparin (2 Units), and 25 microliters of Freund's complete adjuvant. Subsequent injections containing 50 micrograms of hPF4 and 2 Units of heparin in PBS were administered via the IP or tail vein on Days 12, 30, 41 and 48 and 62. Mice were given an intravenous boost of heparin and hPF4 on Day 66, three days prior to sacrifice. Titers of anti-hPF4/heparin were monitored using the ELISA method described below. The two mice expressing the highest serum titers (>1:100,000) of antibodies to hPF4/heparin complex antibodies were sacrificed and their spleens were removed for fusion.

Development of Monoclonal Antibodies

Fusion and hybridoma selection were optimized using standard methodology (Lane et al. 1986, Methods Enzymol 121:1183). Hybridomas were cultured for 7 days and their supernatants screened for antibodies to hPF4/heparin and hPF4 by ELISA. Wells considered positive ($A_{405}$>0.8) were weaned from HAT supplement over 7-10 days, subcloned by limiting dilution, and grown in pristane primed mice to generate ascites. Monoclonal antibodies to hPF4/heparin (KKO) and hPF4 alone (RTO) were isolated from ascitic fluid using the Hi Trap® affinity columns according to the manufacturer's instructions. Isotyping was performed using the ImmunoPure® Monoclonal Antibody Isotyping kit according to the manufacturer's instructions.

Preparation of Human and Murine PF4, hPF4 Mutants, NAP-2, and IL-8

Recombinant wild-type human and mouse PF4, mutant hPF4, and hNAP-2 and hIL-8 were expressed in *E. coli* as described in Park et al., 1990, Blood 75:1290. Briefly, cDNA constructs for each chemokine (see discussion below) were inserted in a pT7-7 vector, introduced into *E. coli* BL21(DE3) pLysS, and grown in Luria broth containing 100 micrograms per milliliter ampicillin. Bacteria were grown to an $A_{600}$ of 1.0 followed by a 3-hour induction at 37° C. with 1 millimolar IPTG. Bacteria were lysed and sonicated, and the chemokine was purified at room temperature by affinity chromatography using heparin-agarose equilibrated with 50 millimolar Tris HCl, 1 millimolar EDTA, pH 8, and eluted using a gradient from 0.2 to 2.0 molar NaCl. Eluted proteins were further purified by reverse-phase chromatography using a ProRPC FPLC column.

Protein purity was assessed using 15% (w/v) sodium dodecyl sulfate (SDS)-polyacrylamide gel electrophoresis followed by Coomassie blue staining (Park et al., 1990, Blood 75:1290). Samples were also subjected to immunoblotting after electrotransfer to polyvinylidenedifluoride (PVDF) membranes using a commercial rabbit anti-hPF4, anti-hNAP-2 or anti-hIL-8 polyclonal antibody, followed by swine anti-rabbit secondary antibody conjugated to horseradish peroxidase. Proteins were detected by ECL as described by the manufacturer. Protein concentrations were determined by the bicinchoninic acid (BCA) assay using BSA as the standard according to the manufacturer's instructions.

Recombinant hPF4 variants were generated using overlap PCR as previously described in Ziporen et al., 1998, Blood 92:3250. These constructs used wild-type hPF4 cDNA as templates and VENT polymerase enzyme. The sequence of each mutant construct was verified using the Sequenase T7 DNA Polymerase Kit. Several new hPF4 constructs were generated, designated P37N, T38Q, A39V, L41V, N47D PF4, that refer to specific amino acids in the 3rd domain of PF4 that were switched individually to those found in hNAP-2.

The cDNA corresponding to the coding region of mature murine PF4 (mPF4) was derived from sequencing an isolated murine lambda FIX 129 SV library clone using human PF4 cDNA as a probe. The coding primers for mPF4 were used to amplify mPF4 cDNA from murine platelet RNA by RT-PCR. Mature mPF4 cDNA was subcloned into pT7-7 vector with an ATG added in-frame at its N-terminus. cDNAs encoding for mature NAP-2 and IL-8 were based on previously published sequences and isolated cDNAs (Ziporen et al., 1998, Blood 92:3250; Baggiolini et al. 1989, J. Clin. Invest. 84:1045).

ELISA Method for Detecting Antibodies to PF4/Heparin Complex

The binding of antibody to either PF4, PF4 variants, PF4 bound to various GAGs or other chemokines complexed to heparin, was measured using an ELISA-based method as previously described (Arepally et al., 1995, Am. J. Clin. Pathol. 104:648). Briefly, to screen hybridoma culture supematants, 96-well microtiter plates were coated overnight at room temperature with 50 micoliters per well of phosphate buffered saline (PBS) containing PF4 (final concentration 10 micrograms per milliliter) in the presence or absence of heparin (0.2 Units/milliliter). The plates were then washed three times with TBS/0.01% Tween-20, blocked with 10% fetal calf serum (FCS) (200 microliters per well) in PBS for 2 hours at room temperature, and washed once more. Culture supernatant was added (50 microliters per well) for 1 hour at room temperature. Non-bound antibody was removed by washing, and 50 microliters per well of alkaline-phosphatase conjugated goat anti-mouse IgG, diluted 1:1000 in 10% FCS/PBS was added for 1 hour at room temperature. After washing, 50 microliters per well of Sigma Fast™ p-nitrophenyl phosphate substrate was added, and the absorbance at 405 nanometers was measured. The binding of KKO to PF4 and related chemokines and the binding of KKO to PF4 bound to various GAGs, was measured in the same manner, except that an incubation volume of 100 microliters per well was used.

Competition Assays by ELISA

The capacity of KKO to bind to wells coated with hPF4/heparin complex in the presence of HIT sera obtained from HIT patients was assessed using a concentration of KKO (diluted in 10% FCS/PBS) which provided 75% of maximal binding. The diluted KKO was added to wells in the presence of varying concentrations of HIT/HITT sera. The binding of KKO to hPF4/heparin complex was measured using the ELISA procedure described above.

Cell Associated ELISA

Cultured human umbilical vein endothelial cells (HWVECs) were prepared as described in Jaffe et al., 1973. J. Clin. Invest. 52:2745. Cells were grown to confluence in complete media containing M199 supplemented with 20% FCS, 100 micrograms per milliliter, penicillin, 100 micrograms per milliliter, streptomycin, 5 micrograms per milliliter, amphotericin B, endothelial cell growth supplement and heparin (100 micrograms per milliliter) in 75 cm² flasks. The cells were then seeded onto 96 well microtiter plates (Jaffe et al., J. Clin. Invest. 52:2745) at a density of 32,000 cells per well in the absence of heparin. After 48 hours in heparin-free medium, the cells were fixed with 0.05% glutaraldehyde and the binding of KKO to the cells or RTO was measured by the ELISA method described above. In other experiments, the binding of KKO to CHO cells lacking xylosyl transferase (provided by. C. Esko, Univ. CA and K. Williams, Thomas Jefferson Univ.) was conducted in essentially the same manner.

Platelet Activation by KKO

Platelet activation by KKO in the presence of PF4 and heparin was assayed by the release of $^{14}C$-serotonin, with modification for a microtiter well format. Briefly, citrated platelet rich plasma obtained from aspirin-free healthy donors was labeled with $^{14}C$-serotonin (22.5 nCi/mL PRP) for 30 minutes at 37° C., after which platelet uptake of $^{14}C$-serotonin was blocked by addition of excess imipramine (1 micromolar final concentration). KKO or isotype control (30-320 micrograms per milliliter) in modified Tyrode's buffer (137 mM NaCl, 3 mM KCl, 0.4 mM $NaH_2PO_4$, 12 mM $NaHCO_3$, and 1 mM $MgCl_2.6H_2O$, pH 7.0) was pre-incubated with either hPF4 (10 micrograms per milliliter) alone, heparin alone (0.2 U/mL), or h-PF4 (10 micrograms per milliliter) plus heparin (0-100 U/mL). Labeled platelets (75 microliters) were added in triplicate to wells containing antigen/antibody-containing mixture (20 microliters) with 5 microliters heparin or buffer to yield a 100 microliters final volume. After a 1 hr incubation at RT, the reaction was terminated by the addition of 100 microliters of 0.5% NaEDTA (pH, 8.5), platelets pelleted and release of $^{14}C$-serotonin measured by liquid scintillation. In other experiments, $^{14}C$-labeled platelets were incubated with the Fc-gamma RIIA blocking antibody mAb IV.3 (7.2 or 72 micrograms per milliliter) for 1 hour prior to the addition of KKO (250 micrograms per milliliter), PF4 and heparin. Controls for the assay included plasma from HIT patients (SRA+, positive control), normal plasma, $mIgG_2b$ (isotype control), RTO and calcium ionophore A23187.

Sequence Analysis of KKO and RTO

Total RNA was prepared from approximately $4 \times 10^6$ hybridoma cells for clones KKO and RTO (TRIzol reagent) followed by cDNA synthesis primed with oligo dT (Superscript Preamplification kit) following the manufacturer's instructions. Heavy and light chain immunoglobulin variable regions were amplified using the polymerase chain reaction as previously described in Siegel et al., 1994, Blood 83:2334 using the following framework 1 and constant region primers for murine gamma and kappa chains: heavy chain forward 5'-GAGGTGAAGCTGGTGGAG(T/A)C(T/A)GG-3' (SEQ ID NO:5), heavy chain reverse 5'-GGGGCCAGTGGATA-GAC-3' (SEQ ID NO:6), light chain forward 5'-CCAGTTC-CGAGCTCCAGATGACCCAGACTCCA-3' (SEQ ID NO:7), light chain reverse 5'-GTTGGTGCAGCATCAGC-3' (SEQ ID NO:8). The PCR products (350-400 bp) were gel purified by electroelution and directly sequenced using the above oligonucleotides and automated fluorescence sequencing. Use of these "universal" variable region framework 1 primers provided heavy and light chain sequences that began at the eighth and ninth amino acid residues, respectively. To determine the authentic amino acid N-terminal residues for KKO chains, putative leader sequences were determined by searching Genbank for other murine monoclonal antibodies with close homology to KKO. For the heavy and light chains of KKO, sequence accession numbers AF025443 and M20830 provided candidate leader sequences. A set of 5' PCR primers beginning at the 5' end of the leaders were synthesized (5'-ATGGGATGGAGCTATATCATCC-3' (SEQ ID NO:9) for heavy chain; 5'-ATGATGAGTCCTGC-CCAGTTCC-3' (SEQ ID NO:10) for light chain). PCR amplifications of KKO heavy and light chain cDNA were performed using these primers paired with the original set of constant region reverse primers. PCR products of the appropriate size (400-450 bp) were obtained and served as templates to provide full-length variable region KKO sequence. Immunoglobulin gene family assignments for heavy and light chains were determined using the Kabat (Kabat et al., 1991, "Sequences of Proteins of Immunological Interest", 5th ed. Bethesda, National Institutes of Health) and Genbank databases. Alignments of the predicted amino acid sequences were performed using the MacVector software package.

Results

Isolation and Screening of Murine Monoclonal Antibodies

Seven days post-fusion, 128 of 1152 wells contained antibodies specific for either a hPF4/heparin complex or hPF4 alone as determined by ELISA using an $A_{405}$ greater than or equal to 0.8 as an arbitrary cut-off value. Cells were subcultured when their supernatants generated $A_{405}$ ratios to hPF4/heparin complex versus hPF4 alone of greater than 1.5. Cell populations showing the greatest relative specificity for the hPF4/heparin complex versus hPF4 alone, and those with high reactivity to hPF4 alone, underwent three additional rounds of subcloning. Two monoclonal antibodies, an $IgG_{2b}\kappa$ antibody specific for the hPF4/heparin complex designated KKO and an $IgG_{2b}\kappa$ antibody specific for hPF4 alone designated RTO, were ultimately isolated and subjected to further characterization. KKO exhibited an $A_{405}$ ratio of greater than 30 to hPF4/heparin complex versus hPF4 alone, whereas RTO demonstrated an $A_{405}$ ratio of less than or equal to 1. These monoclonal antibodies were purified from ascites and were used for all subsequent studies.

Specificity of KKO and RTO for PF4/Heparin Complexes

KKO bound to hPF4/heparin complexes in a dose-dependent manner, as shown in FIG. 1A. Half-maximal binding was exhibited at an antibody concentration of 0.036 micrograms per milliliter. The relative specificity of KKO was determined by adding various dilutions of KKO to wells coated with hPF4/heparin complex or hPF4 alone. Specificity for the complex was evident at all antibody concentrations tested from 0.007 to 36 micrograms per milliliter (FIG. 1A). At concentrations less than 0.14 micrograms per milliliter, the ratio of binding of KKO to PF4/heparin complex vs. binding to PF4 alone as determined by $A_{405}$ was greater than 400. No binding of KKO to PF4 alone was evident at concentrations less than or equal to 0.072 micrograms per milliliter. KKO did not exhibit binding to immobilized heparin at any concentration tested from 0.007-36 micrograms per milliliter. Whereas KKO demonstrated heparin-dependent binding to hPF4, binding of RTO to hPF4 was unaffected by the presence of heparin at all concentrations of antibody tested (FIG. 1B). Naturally-occurring antibodies in patients with HIT recognize hPF4/heparin complexes formed over a narrow range of molar ratios between the reactants (Kelton et al., 1994, Blood 83:3232).

Figure 1C:
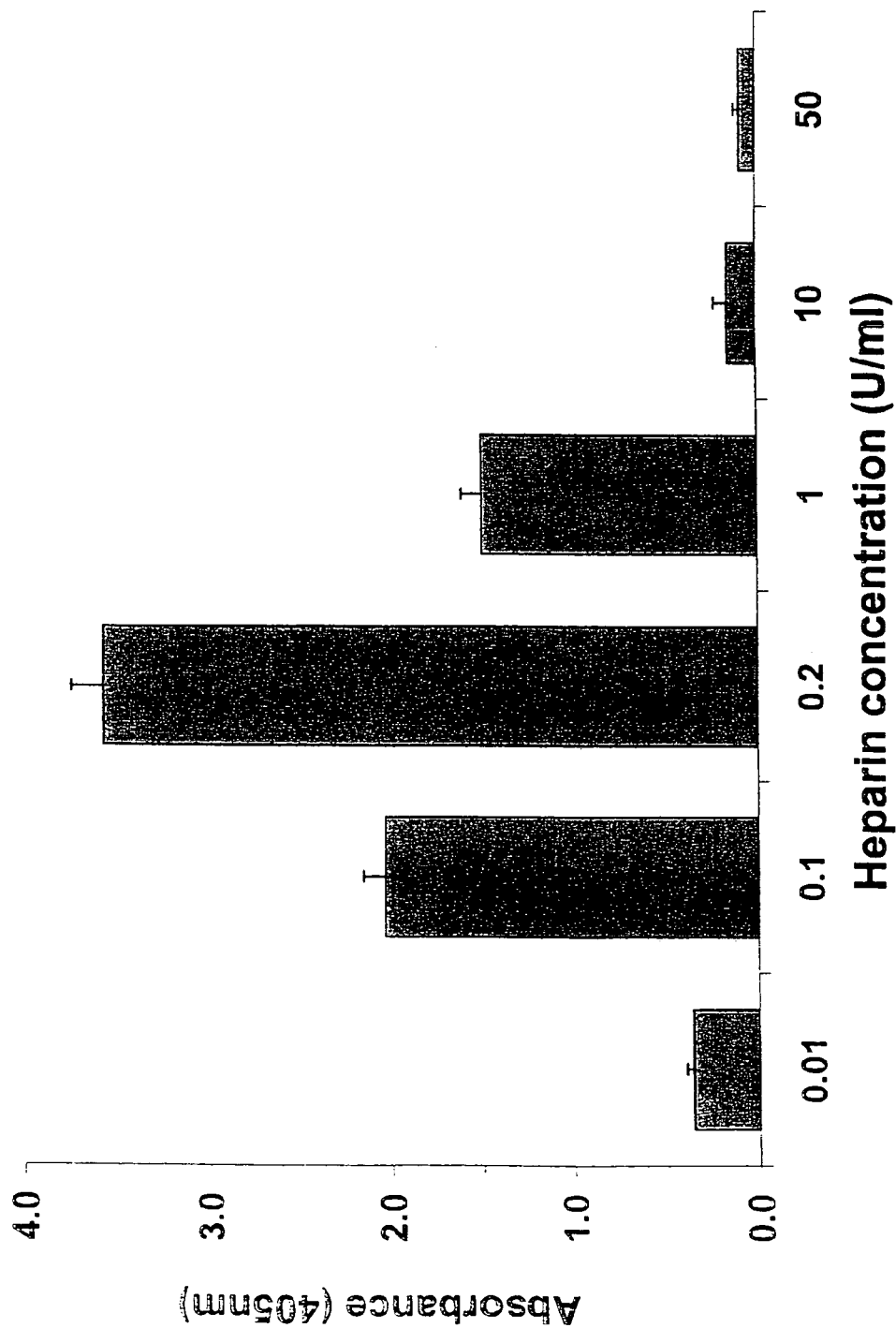

To determine if KKO exhibited similar characteristics, antibody binding to HPF4/heparin complex was measured at a fixed concentration of hPF4 (10 micrograms per milliliter) and varying concentrations of heparin (0.01-50 Units/mL). Optimal binding of KKO occurred at a molar ratio of hPF4 to heparin of 3:1. Reduced KKO binding to hPF4/heparin complex was observed in the presence of higher and lower concentrations of heparin (FIG. 1C).

Binding of KKO to Human PF4 in Complex with GAGs

Another feature of naturally-occurring HIT antibodies is their cross-reactivity with complexes composed of PF4 and other sulfated glycosaminoglycans (GAGs) (Greinacher et al., 1992, Thromb. Haemost. 67:545; Greinacher et al., 1995, Thromb. Haemost. 74:886). As shown in FIG. 2, KKO bound to complexes formed between hPF4 (10 micrograms per milliliter) and 0-500 micrograms per milliliter chondroitin sulfate A, chondroitin sulfate B or dermatan sulfate, chondroitin sulfate C, heparan sulfate and dextran sulfate ($M_r$ 8000), in a pattern of binding similar to that reported previously for HIT antibodies (Greinacher et al., 1994, Thromb. Haemost. 71:247).

Cell-Reactivity of KKO

Similar to HIT-IgG (Visentin et al., 1994, J. Clin. Invest. 93:81), KKO bound to cultured endothelial cells (FIG. 3) and CHO cells in the presence of exogenous hPF4, but not to CHO cells lacking heparan sulfate- or chondroitin sulfate-containing proteoglycans under the sane conditions. Binding of KKO to HUVECs was inhibited by heparin at concentrations (0.2 Units/mL) known to dissociate PF4 from the cell surface. In comparison to KKO, equimolar concentrations of RTO bound one-third as well to HUVEC in the presence of either PF4 or PF4 and heparin, consistent with ELISA data shown in FIGS. 1A and 1B. Whereas binding of KKO to PF4 was enhanced in the presence of heparin (FIG. 1A), binding of RTO was diminished (FIG. 1B), suggesting that RTO recognizes an epitope on PF4 that is masked or altered by heparin or heparin-like molecules upon formation of the PF4/heparin complex.

Platelet Activation by KKO

Figure 4:
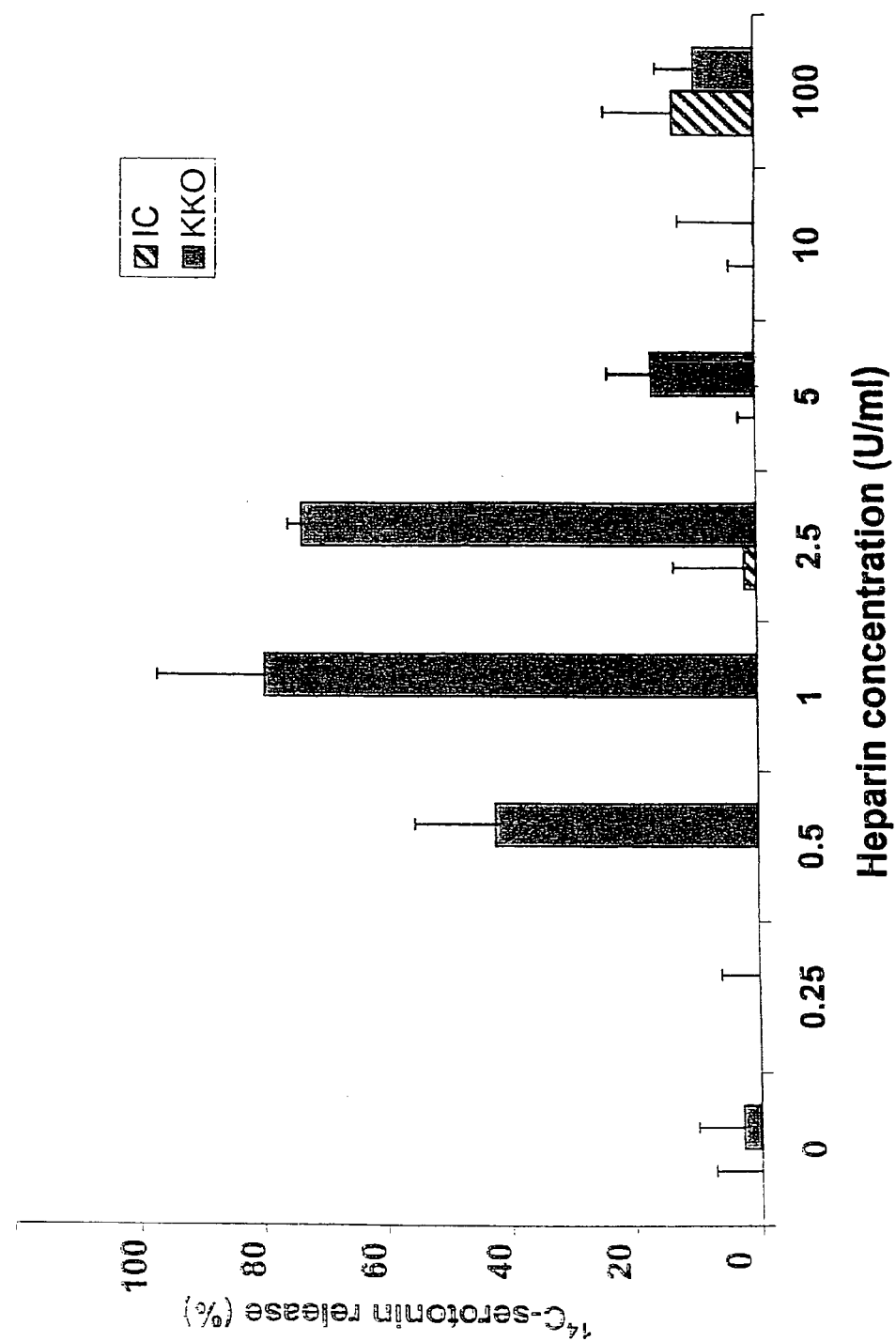
FIG. 4 is a graph depicting heparin dependent $^{14}C$-serotonin release stimulated by KKO. $^{14}C$-labeled platelet rich plasma was incubated with 80 micrograms per milliliter of either KKO or isotype control antibody (IC) in the presence of hPF4 (10 micrograms per milliliter) and subsequently added to wells containing labeled platelets with the indicated concentrations of heparin. The data presented represent the mean±1 standard deviation of triplicate measurements and are representative of at least three independent measurements.

HIT antibodies (Kelton et al., 1988, Blood 72:925), and immune complexes containing murine $IgG_2$ antibodies activate human platelets through a process which requires Fc-gamma RIIA (Hewlett et al., 1994, Adv. Immunol 57:1; De Reys et al., 1993, Blood 81:1792). In order to determine whether KKO activates platelets through a similar pathway, $^{14}C$-serotonin-labeled platelets were incubated with KKO (at concentrations ranging from 30 to 320 micrograms per milliliter) in the presence of either hPF4 alone, heparin alone, or hPF4/heparin complex. KKO at concentrations of 80 and 160 micrograms per milliliter) stimulated $^{14}C$-serotonin release in a heparin-dependent manner as shown in FIG. 4 when pre-incubated with 10 micrograms per milliliter of hPF4. Somewhat higher concentrations of antibody (KKO greater than 180 micrograms per milliliter) were required to initiate serotonin release when the antibody was pre-incubated with 10 micrograms per milliliter of hPF4 complexed to heparin (1 Unit/mL). Neither KKO nor the isotype control activated platelets in the presence of buffer alone or heparin alone. The release of $^{14}C$-serotonin induced by KKO was almost completely inhibited by the FcγRIIA-specific mAb IV.3 (less than 5% release at 0.5, 1, and 5 Units/mL heparin). RTO did not exhibit the ability to effect serotonin release in the presence or absence of hPF4 alone or hPF4/heparin complex at all concentrations tested (from 31-250 micrograms per milliliter).

Epitope Specificity of KKO

It has been reported that a subset of HIT/HITT antibodies require an epitope in the 3rd domain of hPF4 in order to bind hPF4 in the presence of heparin. This region was defined using chimeras between hPF4 and the structurally related chemokine, NAP-2, which is not recognized by HIT antibodies (Ziporen et al., 1998, Blood 92:3250). In order to investigate both the specificity of this subset of HIT antibodies in greater detail and the involvement of this domain in the binding of KKO, single amino acid substitutions were introduced into the 3rd domain of PF4, between Cys36 and Cys52. Each PF4 variant was incubated with an optimal concentration of heparin (Ziporen et al., 1998, Blood 92:3250) and the binding of KKO with sera obtained from 23 HIT patients was assessed.

The binding of HIT antibodies to heparin complexed with the PF4 variants P37N, T38Q, A39V, L41 V, and N47D was moderately impaired, compared with wild type PF4, whereas binding to NAP-2 was minimal. Binding of HIT antibodies to the hPF4 variants exhibited greater variability than binding to wild type hPF4, suggesting differences in the proportion of antibodies in individual sera sensitive to changes in the third domain of hPF4. HIT sera could be divided arbitrarily into subgroups exhibiting marked ($A_{405}$ of less than 1.0), intermediate ($A_{405}$ greater than or equal to 1.0 to less than 2.5), or little ($A_{405}$ of greater than 2.5), sensitivity to the P37N mutation. The binding of HIT antibodies to PF4 variants having mutations in the 3rd domain (T38Q, A39V, L41V, and N47D) generally displayed the same pattern of reactivity (i.e., sera containing antibodies which recognized P37N also recognized T38Q, etc.). These data suggest that there are at least two antigenic sites recognized by antibodies in sera obtained from patients with HIT. Sera from most HIT patients contain antibodies which recognize both sites, but a subgroup are comprised of antibodies which predominantly recognize an antigenic site (or sites) involving the 3rd domain of hPF4.

Figure 5A:
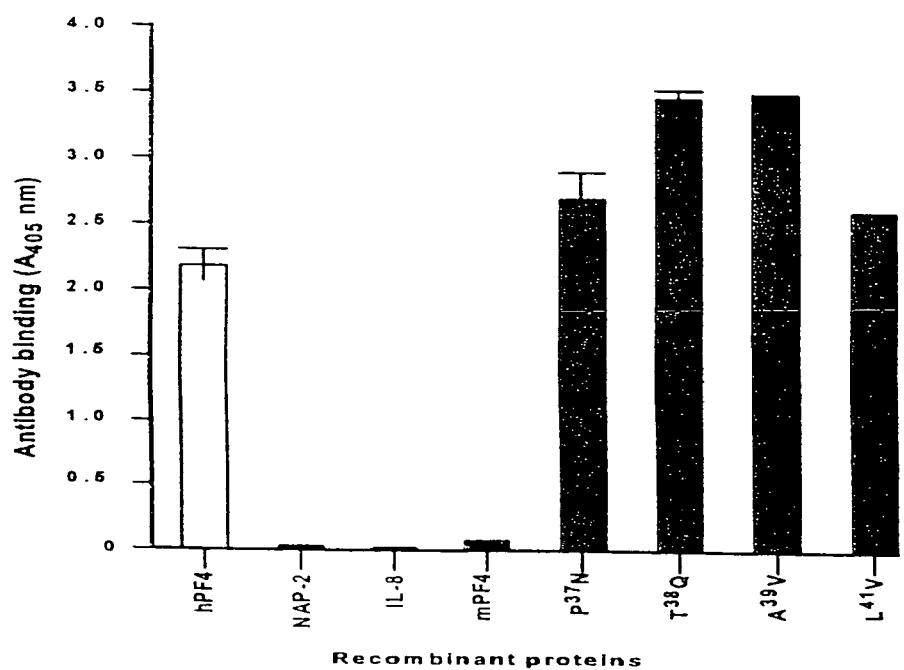
FIGS. 5A and 5B, is a pair of graphs which depict the characterization of the KKO binding site on the hPF4/heparin complex.

The antigenic site recognized by KKO was characterized next. It has been reported previously that greater than 95% of HIT antibodies do not recognize IL-8 or NAP-2 complexed to heparin (Ziporen et al., 1998, Blood 92:3250; Amiral et al., 1996, Blood 88:410), although IL8 and NAP-2 share about 30% and about 60% amino acid sequence homology, respectively, with hPF4. KKO shares this characteristic and does not bind to either chemokine when complexed to heparin, as shown in FIG. 5A. Secondly, none of the 23 HIT sera tested or KKO reacted with murine PF4 complexed to heparin (FIG. 5A), in spite of mPF4 displaying, about 80% amino acid sequence identity with its human homologue. Thirdly, KKO bound strongly to the PF4 variants P37N, T38Q, A39V and L41V in the presence of heparin (FIG. 5A), similar to the behavior of the sub-group of HIT sera characterized as "insensitive" to mutations in the third domain.

Figure 5B:
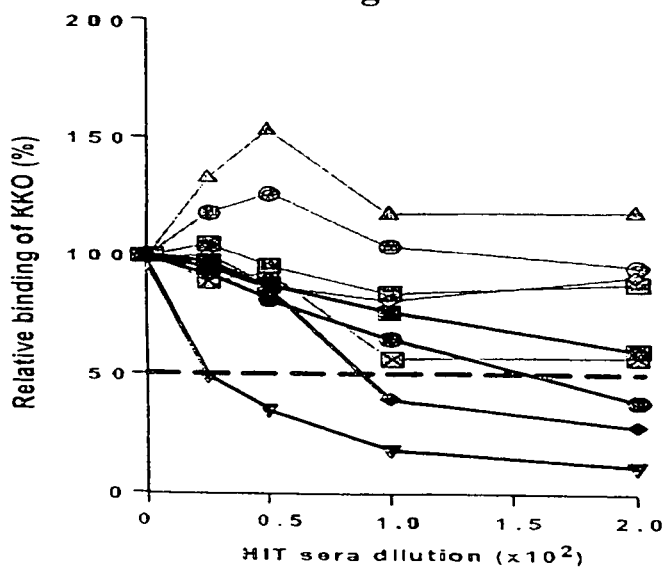

In light of these findings, cross-competition experiments were then performed to determine whether KKO and this subset of HIT antibodies recognized an overlapping site in PF4. To do so, the binding of KKO to hPF4/heparin complex was measured in the presence of increasing amounts of four 3rd-domain "insensitive" HIT sera and five "sensitive" sera (FIG. 5B). Three of four "insensitive" serum samples tested inhibited the binding of KKO to hPF4/heparin complex by about 50%. In contrast, none of the 5 sera designated "sensitive" inhibited binding of KKO to a similar extent. These data are consistent with the pattern of KKO binding to the 3rd domain mutants shown in FIG. 5A and suggest that KKO recognizes an epitope of the hPF4/heparin complex which overlaps with one recognized by a subset of HIT antibodies.

Sequence Analysis of KKO and RTO

Figure 6:
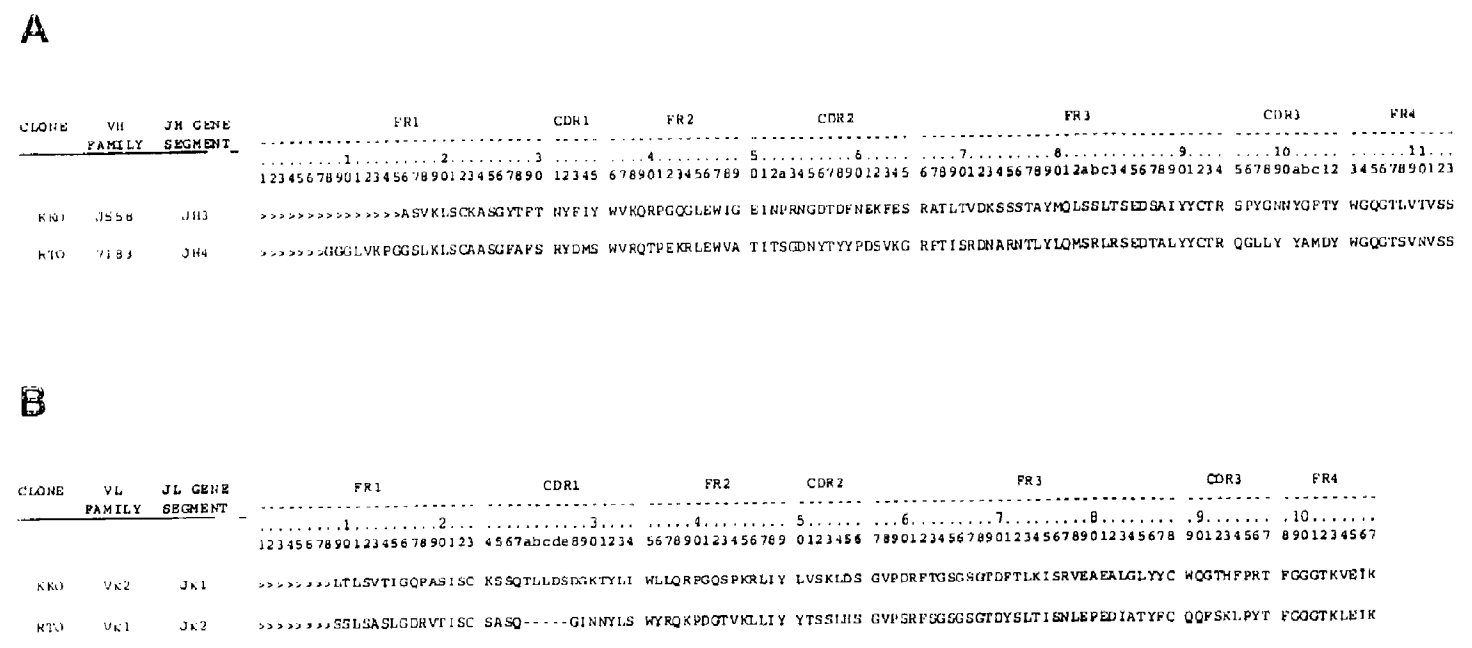

The predicted amino acid sequence of KKO, a PF4/heparin complex-specific murine monoclonal antibody, and RTO, a non-heparin dependent anti-PF4 murine monoclonal antibody were compared. Results are shown in FIGS. 6A and 6B. Sequence analysis revealed the use of very disparate $V_H$ families and $J_H$-gene segments and $V_L$ families and $J_L$ gene segments for KKO (SEQ ID NOs:11 and 13) and RTO (SEQ ID NOs: 12 and 14) heavy and light chains, respectively. Although one cannot rule out similarities in the idiotypes expressed by two antibodies based on their primary heavy and light chain sequences, it is clear that KKO and RTO are not genetically (or clonally) related, nor do they bear any obvious predicted structural homology to each other.

Discussion

A murine monoclonal antibody termed KKO was generated which binds specifically with a PF4/heparin complex and which binds preferentially with the PF4/heparin complex relative to its binding with either PF4 or heparin alone. KKO shares important serologic and functional properties with naturally-occurring anti-PF4/heparin complex antibodies obtained from sera of patients with heparin-induced thrombocytopenia/thrombosis (HITT). KKO recognizes PF4 in complex with heparin over a narrow range of molar ratios approaching 1:1, similar to the behavior of naturally-occurring HIT antibodies (Amiral et al., 1992. Thromb. Haemost 68:95). KKO also binds specifically with complexes between PF4 and other glycosaminoglycans (GAGs), but not with heparin itself, or with heparin complexed with either mPF4, NAP-2, or IL-8. These features are shared with greater than 95% of HIT antibodies. KKO binds to cells which express GAGs (such as endothelial cells) only when PF4 is provided exogenously (Herbert et al., 1998, Thromb. Haemost 80:326; Visentin et al., 1994, J. Clin. Invest. 93:81; Tannenbaum et al., 1986, J. Immunol 137:1532). It does not bind to cells which lack GAGs and which are therefore unable to form the requisite antigenic complex. KKO also activates human platelets through a heparin- and PF4-dependent mechanism that is mediated through Fc-gamma RIIA (Kelton et al., 1988, Blood 72:925).

The binding of KKO to the PF4/heparin complex exceeded binding of KKO to PF4 alone by greater than 400 fold under optimal binding conditions. However, the finding that KKO binds to PF4 at high concentrations of KKO is consistent with the hypothesis that heparin and other GAGs induce a conformational change in the protein which generates neoepitopes within the PF4 molecule which are responsible for antibody formation (Ziporen et al., 1998, Blood 92:3250; Horsewood et al., 1996, Br. J. Haematol. 95:161; Mayo et al., 1995, Biochem J. 312:357). The fact that mice injected with heparin and PF4 generate PF4/heparin complex-specific antibodies indicated the immunogenicity of these putative neoepitopes and may have implications for the mechanism by which antibody formation is stimulated in humans.

The results of several studies have indicated that naturally-occurring antibodies specific for the PF4/heparin complex are polyspecific (Suh et al., 1998, Blood 91:916; Ziporen et al., 1998, Blood 92:3250). KKO competes with a subset of these antibodies for binding to the PF4/heparin complex. A region has previously been identified in the 3rd domain of PF4 which is required for recognition by a subset of HIT/HITT antibodies (Ziporen et al., 1998, Blood 92:3250). Additional mutations in this region affirm its contribution to the immunodominant epitope recognized by some, but not other, naturally-occurring antibodies. The results of direct binding studies using these variant PF4 molecules, as well as competition studies using HIT/HITT sera subdivided by their capacity to recognize these variants, suggest that the epitope for KKO lies outside of this third domain. A comparison of the amino acid sequences of KKO, a PF4/heparin complex-specific antibody, with RTO, a PF4-specific antibody, fails to suggest any obvious genetic relatedness or structural similarity between the combining regions of these antibodies or any relationship between their binding sites on PF4.

The propensity of patients with HIT to develop thrombosis has been attributed to antibody-mediated platelet activation in vivo (Kelton et al., 1988, Blood 72:925; Fratantoni et al., 1975, Blood 45:395). Interestingly, the concentrations of KKO required to activate platelets (i.e., at least 80 micrograms per milliliter) greatly exceed the minimal amount of KKO required to detect the PF4/heparin complex by ELISA (0.036 micrograms per milliliter). In addition to reflecting the difference in sensitivity of these two assays (Bauer et al., 1997, Circulation 95:1242; Visentin et al., 1996, J. Lab. Clin. Med. 128:376), this finding might indicate a threshold of Fc receptor occupancy that must be exceeded in order for KKO to initiate platelet activation. Naturally-occurring differences, either in the expression of FcγRIIA (Rosenfeld et al., 1987, J. Immunol 138:2869: McCrae et al., 1990, J. Immunol. 144: 3920), the extent to which receptor expression is upregulated when platelets are activated (McCrae et al., 1990, J. Immunol. 144:3920; Chong et al., 1993, Blood 81:988), the presence of higher titers of IgG antibodies in patients with thrombosis (Suh et al., 1997, Am. J. Hematol. 54:196), or the poorly understood role of the platelet Fc-gamma RIIA-H/R$^{131}$ polymorphism, may each contribute to the propensity of some patients with sensitization to the PF4/heparin complex to develop overt disease. Platelet activation by KKO may be limited both by the number and conformation of the PF4/heparin complexes which can bind to the platelet surface, and by the affinity of murine IgG$_{2b}$ for human Fc-gamma RIIA.

Although the relationship between plasma PF4/heparin complex-specific antibodies and HIT is well established, there is no formal proof that these antibodies, or a subset of these antibodies, actually cause thrombocytopenia or thrombosis. It has been reported previously that mice immunized with HIT-IgG develop murine antibodies to human PF4/heparin complexes and PF4-dependent endothelial cell-reactive antibodies as part of the idiotype/anti-idiotype network (Blank et al., 1997, Clin. Exp. Immunol. 108:333). Immunized mice developed thrombocytopenia when exposed to heparin. However, as these mice likely developed antibodies with additional specificities as a result of epitope spread, the contribution of PF4/heparin complex-specific antibodies per se to the development of thrombocytopenia or thrombosis remains unproven. PF4/heparin complex-specific monoclonal antibodies such as KKO facilitate efforts to identify the pathophysiological role of anti-PF4/heparin complex antibodies in vivo. It is also anticipated that KKO and related antibodies will be useful to elucidate the physiologic role of PF4 in hemostasis, serve as a reagent standard in methods for diagnosing HIT/HITT, and may provide a platform from which to identify therapeutic alternatives for patients with HIT/HITT.

Example 2

The experiments described in this Example provide evidence that KKO, a murine monoclonal antibody of the invention, induces the secretion of IL-8 by monocytes in the presence of PF4, but not in the presence of heparin alone or a PF4/heparin complex. The cytokine IL-8 is often used as a surrogate marker for activated monocytes and monocyte-like cells.

Using the monocytic cell line U937, various treatments with stimulants were tested in the cells (no stimulant, TNF-alpha, KKO, an isotype control antibody TRA-2b, sera from a patient with HIT, and sera from a control patient) in the presence of either PF4 (10 micrograms per milliliter), heparin (1 Unit per milliliter) or the PF4/heparin complex (10 micrograms per milliliter and 1 Unit per milliliter, respectively). The cells were cultured for 24 hours with the various stimulants, and the secretion of IL-8 was measured using a commercially available assay (R&D Systems, Minneapolis, Minn.).

Figure 8:
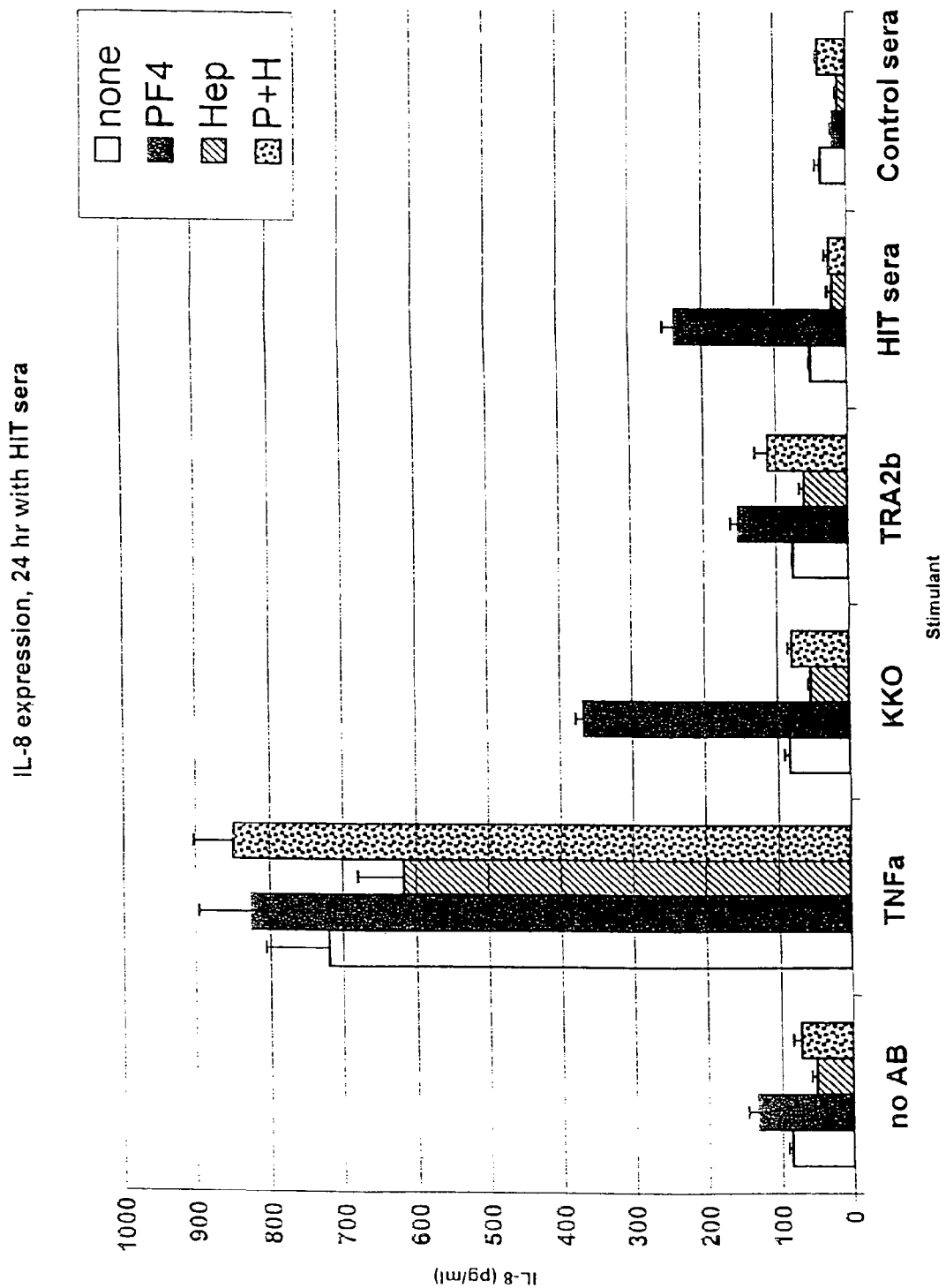
FIG. 8 is a graph depicting the level of IL-8 secretion in the monocytic cell line U937 after incubation of the cells for 24 hours with either no stimulant (no antibody) or a stimulant selected from the group consisting of TNF-alpha (TNFa), the murine monoclonal antibody KKO (KKO), an isotype control antibody (TRA2b), sera from a patient with HIT (HIT sera) and control sera (control sera). The level of IL-8 secretion is expressed in picograms per milliliter.

As depicted in FIG. 8, a significant amount of IL-8 secretion by the cells was observed, which was increased in the presence of PF4 with KKO relative to the isotype control antibody, and with HIT sera as compared to control sera. Without wishing to be bound by any particular theory, it is suspected that KKO binds with PF4 complexed to cell surface glycosaminoglycans, which leads to the activation of monocyte-like cells. These results are similar to findings which indicate increased IL-8 secretion by HIT sera relative to control sera.

These data provide evidence that the murine monoclonal antibody of the invention KKO participates in the pathogenesis of HIT/HITT. Since KKO binds and activates monocytes, tissue factor expression may be increased by KKO, which promotes the hypercoagulable state of HIT/HITT. The activation of monocytes by HIT/HITT antibodies can be used as a diagnostic marker, and the blocking of monocyte activation by a monoclonal antibody of the invention such as KKO or a derivative thereof can be used therapeutically to halt the development of thrombosis.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A Fab antibody capable of binding specifically with a platelet factor 4 (PF4)/heparin complex, wherein said antibody preferentially binds with said PF4/heparin complex relative to the binding of said antibody with either PF4 or heparin alone, wherein the Fab antibody comprises an antibody-binding fragment comprising the amino acid sequence of SEQ ID NO: 11, and wherein the Fab antibody further comprises the amino acid sequence of SEQ ID NO:13.

2. A kit for diagnosing HIT/HITT in a mammal, said kit comprising:
 (a) a positive control solution comprising a monoclonal antibody or antigen-binding fragment thereof which binds specifically with a platelet factor 4 (PF4)/heparin complex, wherein said monoclonal antibody or antigen-binding fragment thereof preferentially binds with said PF4/heparin complex relative to the binding of said monoclonal antibody or antigen-binding fragment thereof with either PF4 or heparin alone, and wherein the monoclonal antibody or antigen-binding fragment thereof comprises the amino acid sequence of SEQ ID NO: 11 and the amino acid sequence of SEQ ID NO:13; and
 (b) an instructional material describing the use of said positive control solution for diagnosing HIT/HITT in a mammal.

3. The kit of claim 2 wherein the monoclonal antibody is produced by hybridoma KKO deposited under ATCC Accession No: PTA-6133.

4. A kit for diagnosing HIT/HITT in a mammal, said kit comprising:
 (a) a positive control solution comprising a monoclonal antibody or an antigen-binding fragment thereof which binds specifically with a platelet factor 4 (PF4)/heparin complex, wherein said monoclonal antibody or antigen-binding fragment thereof preferentially binds with said PF4/heparin complex relative to the binding of said monoclonal antibody or antigen-binding fragment thereof with either PF4 or heparin alone, and wherein the monoclonal antibody is produced by hybridoma KKO deposited under ATCC Accession No: PTA-6133; and
 (b) an instructional material describing the use of said positive control solution for diagnosing HIT/HITT in a mammal.

* * * * *

SEQUENCE LISTING

<160> NUMBER OF SEQ ID NOS: 14

<210> SEQ ID NO 1
<211> LENGTH: 120
<212> TYPE: PRT
<213> ORGANISM: Mus musculus

<400> SEQUENCE: 1

Glu Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Thr Asn Tyr
            20                  25                  30

Phe Ile Tyr Trp Val Lys Gln Arg Pro Gly Gln Gly Leu Glu Trp Ile
        35                  40                  45

Gly Glu Ile Asn Pro Arg Asn Gly Asp Thr Asp Phe Asn Glu Lys Phe
    50                  55                  60

```
Glu Ser Arg Ala Thr Leu Thr Val Asp Lys Ser Ser Thr Ala Tyr
65                  70                  75                  80

Met Gln Leu Ser Ser Leu Thr Ser Glu Asp Ser Ala Ile Tyr Tyr Cys
                85                  90                  95

Thr Arg Ser Pro Tyr Gly Asn Asn Tyr Gly Phe Thr Tyr Trp Gly Gln
            100                 105                 110

Gly Thr Leu Val Thr Val Ser Ala
        115                 120

<210> SEQ ID NO 2
<211> LENGTH: 110
<212> TYPE: PRT
<213> ORGANISM: Mus musculus

<400> SEQUENCE: 2

Ala Glu Leu Asp Ile Gln Met Ile Gln Ser Gln Lys Phe Met Ser Thr
1               5                   10                  15

Ser Val Gly Asp Arg Val Thr Val Thr Cys Lys Ala Ser Gln Asn Val
            20                  25                  30

Gly Thr Asn Val Ala Trp Tyr Gln Gln Lys Pro Gly Gln Ser Pro Asn
        35                  40                  45

Ala Leu Ile Tyr Ser Ala Ser Tyr Arg Tyr Ser Gly Val Pro Asp Arg
    50                  55                  60

Phe Thr Gly Ser Gly Ser Gly Thr Asp Phe Thr Leu Thr Ile Thr Asn
65                  70                  75                  80

Val Gln Ser Glu Asp Leu Ala Asp Tyr Phe Cys Gln Gln Tyr Asn Ser
                85                  90                  95

Tyr Pro Leu Thr Phe Gly Thr Gly Thr Lys Leu Glu Ile Lys
            100                 105                 110

<210> SEQ ID NO 3
<211> LENGTH: 360
<212> TYPE: DNA
<213> ORGANISM: Mus musculus

<400> SEQUENCE: 3
gaggttcagc tgcagcagtc tggggctgaa ctggtgaagc ctggggcttc agtgaagttg      60
tcctgtaagg cttctggcta caccttcacc aattacttta tactgggt gaagcagagg      120 cctggacaag gccttgagtg gattggagag attaatccta gaaatggtga tactgacttc      180
aatgagaagt tcgagagcag ggccacactg actgtagaca atcctccag cacggcatac      240 atgcaactca gcagcctgac atctgaggac tctgcgatct attactgtac aagatccccc      300
tacggtaata actacgggtt tacttactgg ggccaaggga ctctggtcac tgtctctgca      360

<210> SEQ ID NO 4
<211> LENGTH: 330
<212> TYPE: DNA
<213> ORGANISM: Mus musculus

<400> SEQUENCE: 4
gccgagctcg atattcagat gattcagtct caaaaattca tgtccacatc agtaggagac      60
agggtcaccg tcacctgcaa ggccagtcag aatgtgggta ctaatgtagc ctggtatcaa      120
cagaaaccag ggcaatctcc taatgcactg atttactcgg catcctaccg gtacagtgga      180
gtccctgatc gcttcacagg cagtggatct gggacagatt tcactctcac catcaccaat      240
gtgcagtctg aagacttggc agactatttc tgtcagcaat ataacagcta tcctctcaca      300
```
ttcggtactg gcaccaaact ggaaatcaaa                                    330

<210> SEQ ID NO 5
<211> LENGTH: 23
<212> TYPE: DNA
<213> ORGANISM: Artificial Sequence
<220> FEATURE:
<223> OTHER INFORMATION: primer

<400> SEQUENCE: 5
gaggtgaagc tggtggagwc wgg                                           23

<210> SEQ ID NO 6
<211> LENGTH: 17
<212> TYPE: DNA
<213> ORGANISM: Artificial Sequence
<220> FEATURE:
<223> OTHER INFORMATION: primer

<400> SEQUENCE: 6
ggggccagtg gatagac                                                  17

<210> SEQ ID NO 7
<211> LENGTH: 32
<212> TYPE: DNA
<213> ORGANISM: Artificial Sequence
<220> FEATURE:
<223> OTHER INFORMATION: primer

<400> SEQUENCE: 7
ccagttccga gctccagatg acccagactc ca                                 32

<210> SEQ ID NO 8
<211> LENGTH: 17
<212> TYPE: DNA
<213> ORGANISM: Artificial Sequence
<220> FEATURE:
<223> OTHER INFORMATION: primer

<400> SEQUENCE: 8
gttggtgcag catcagc                                                  17

<210> SEQ ID NO 9
<211> LENGTH: 22
<212> TYPE: DNA
<213> ORGANISM: Artificial Sequence
<220> FEATURE:
<223> OTHER INFORMATION: primer

<400> SEQUENCE: 9
atgggatgga gctatatcat cc                                            22

<210> SEQ ID NO 10
<211> LENGTH: 22
<212> TYPE: DNA
<213> ORGANISM: Artificial Sequence
<220> FEATURE:
<223> OTHER INFORMATION: primer

<400> SEQUENCE: 10
atgatgagtc ctgcccagtt cc                                            22

<210> SEQ ID NO 11
<211> LENGTH: 105
<212> TYPE: PRT
<213> ORGANISM: Mus musculus

<400> SEQUENCE: 11

```
Ala Ser Val Lys Leu Ser Cys Lys Ala Ser Gly Tyr Thr Phe Thr Asn
1               5                   10                  15

Tyr Phe Ile Tyr Trp Val Lys Gln Arg Pro Gly Gln Gly Leu Glu Trp
            20                  25                  30

Ile Gly Glu Ile Asn Pro Arg Asn Gly Asp Thr Asp Phe Asn Glu Lys
        35                  40                  45

Phe Glu Ser Arg Ala Thr Leu Thr Val Asp Lys Ser Ser Ser Thr Ala
    50                  55                  60

Tyr Met Gln Leu Ser Ser Leu Thr Ser Glu Asp Ser Ala Ile Tyr Tyr
65                  70                  75                  80

Cys Thr Arg Ser Pro Tyr Gly Asn Asn Tyr Gly Phe Thr Tyr Trp Gly
                85                  90                  95

Gln Gly Thr Leu Val Thr Val Ser Ser
                100                 105
```

<210> SEQ ID NO 12
<211> LENGTH: 112
<212> TYPE: PRT
<213> ORGANISM: Mus musculus

<400> SEQUENCE: 12

```
Gly Gly Gly Leu Val Lys Pro Gly Gly Ser Leu Lys Leu Ser Cys Ala
1               5                   10                  15

Ala Ser Gly Phe Ala Phe Ser Arg Tyr Asp Met Ser Trp Val Arg Gln
            20                  25                  30

Thr Pro Glu Lys Arg Leu Glu Trp Val Ala Thr Ile Thr Ser Gly Asp
        35                  40                  45

Asn Tyr Thr Tyr Tyr Pro Asp Ser Val Lys Gly Arg Phe Thr Ile Ser
    50                  55                  60

Arg Asp Asn Ala Arg Asn Thr Leu Tyr Leu Gln Met Ser Arg Leu Arg
65                  70                  75                  80

Ser Glu Asp Thr Ala Leu Tyr Tyr Cys Thr Arg Gln Gly Leu Leu Tyr
                85                  90                  95

Tyr Ala Met Asp Tyr Trp Gly Gln Gly Thr Ser Val Asn Val Ser Ser
                100                 105                 110
```

<210> SEQ ID NO 13
<211> LENGTH: 104
<212> TYPE: PRT
<213> ORGANISM: Mus musculus

<400> SEQUENCE: 13

```
Leu Thr Leu Ser Val Thr Ile Gly Gln Pro Ala Ser Ile Ser Cys Lys
1               5                   10                  15

Ser Ser Gln Thr Leu Leu Asp Ser Asp Gly Lys Thr Tyr Leu Ile Trp
            20                  25                  30

Leu Leu Gln Arg Pro Gly Gln Ser Pro Lys Arg Leu Ile Tyr Leu Val
            35                  40                  45

Ser Lys Leu Asp Ser Gly Val Pro Asp Arg Phe Thr Gly Ser Gly Ser
    50                  55                  60

Gly Thr Asp Phe Thr Leu Lys Ile Ser Arg Val Glu Ala Glu Ala Leu
65                  70                  75                  80

Gly Leu Tyr Tyr Cys Trp Gln Gly Thr His Phe Pro Arg Thr Phe Gly
                85                  90                  95
```

```
Gly Gly Thr Lys Val Glu Ile Lys
            100

<210> SEQ ID NO 14
<211> LENGTH: 99
<212> TYPE: PRT
<213> ORGANISM: Mus musculus

<400> SEQUENCE: 14

Ser Ser Leu Ser Ala Ser Leu Gly Asp Arg Val Thr Ile Ser Cys Ser
1               5                   10                  15

Ala Ser Gln Gly Ile Asn Asn Tyr Leu Ser Trp Tyr Arg Gln Lys Pro
                20                  25                  30

Asp Gly Thr Val Lys Leu Leu Ile Tyr Tyr Thr Ser Ser Leu His Ser
            35                  40                  45

Gly Val Pro Ser Arg Phe Ser Gly Ser Gly Ser Gly Thr Asp Tyr Ser
        50                  55                  60

Leu Thr Ile Ser Asn Leu Glu Pro Glu Asp Ile Ala Thr Tyr Phe Cys
65                  70                  75                  80

Gln Gln Phe Ser Lys Leu Pro Tyr Thr Phe Gly Gly Gly Thr Lys Leu
                85                  90                  95

Glu Ile Lys
```